US010842966B2

(12) United States Patent
Hochman et al.

(10) Patent No.: US 10,842,966 B2
(45) Date of Patent: Nov. 24, 2020

(54) APPARATUS FOR ASSISTING A USER IN ADVANCING A NEEDLE INTO A SUBJECT AT A SELECTED RATE

(71) Applicant: Milestone Scientific, Inc., Livingston, NJ (US)

(72) Inventors: Mark N. Hochman, Great Neck, NY (US); Leonard A. Osser, Tampa, FL (US)

(73) Assignee: MILESTONE SCIENTIFIC, INC., Roseland, NJ (US)

( * ) Notice: Subject to any disclaimer, the term of this patent is extended or adjusted under 35 U.S.C. 154(b) by 24 days.

(21) Appl. No.: 15/767,186

(22) PCT Filed: Oct. 17, 2016

(86) PCT No.: PCT/US2016/057264
§ 371 (c)(1),
(2) Date: Apr. 10, 2018

(87) PCT Pub. No.: WO2017/066732
PCT Pub. Date: Apr. 20, 2017

(65) Prior Publication Data
US 2018/0296792 A1 Oct. 18, 2018

Related U.S. Application Data

(63) Continuation-in-part of application No. 15/141,231, filed on Apr. 28, 2016, now Pat. No. 10,220,180, (Continued)

(51) Int. Cl.
*A61M 19/00* (2006.01)
*A61B 5/00* (2006.01)
(Continued)

(52) U.S. Cl.
CPC ........... *A61M 19/00* (2013.01); *A61B 5/4896* (2013.01); *A61M 5/16854* (2013.01);
(Continued)

(58) Field of Classification Search
CPC ...... A61M 5/20; A61M 5/427; A61M 5/5086; A61M 5/16854; A61M 5/142;
(Continued)

(56) References Cited

U.S. PATENT DOCUMENTS 3,867,934 A 2/1975 Ollivier
4,356,826 A 11/1982 Kubota
(Continued)

FOREIGN PATENT DOCUMENTS

DE 202005019430 2/2006
EP 0303824 2/1989
(Continued)

OTHER PUBLICATIONS

Gadsden et al., "Opening Injection Pressure Consistently Detects Needle-Nerve Contact during Ultrasound-guided Interscalene Brachial Plexus Block" Anesthesiology, vol. 120, No. 5, May 2014, pp. 1246-1253.
(Continued)

*Primary Examiner* — Laura A Bouchelle
*Assistant Examiner* — Justin L Zamory
(74) *Attorney, Agent, or Firm* — Niels Haun; Dann, Dorfman, Herrell & Skillman, PC

(57) ABSTRACT

A system (5, 405) for infusing medication into a subject is provided. The system (5, 405) includes an injection system (50, 450) for controlling fluid flow from a fluid reservoir to a needle. A sensor (20) detects a characteristic indicative of fluid pressure in the needle. The injection system (50, 450) controls the flow of fluid to the needle in response to the characteristic detected by the sensor (20), which continu-
(Continued)

ously detects the characteristic as the needle is inserted into the subject. The system may include a light assembly (100) connected with the injection system. The light assembly (100) may provide a continuously variable signal indicative of the fluid pressure in the needle. The system (5, 405) may further provide a mechanism that provides cues to the operator to insert the needle at a particular rate. The system may further include a conductive element (334) for providing electric nerve stimulation.

15 Claims, 11 Drawing Sheets

Related U.S. Application Data which is a continuation-in-part of application No. 15/062,685, filed on Mar. 7, 2016, now abandoned.

(60) Provisional application No. 62/242,745, filed on Oct. 16, 2015.

(51) Int. Cl.
| | |
|---|---|
| *A61M 5/168* | (2006.01) |
| *A61M 5/20* | (2006.01) |
| *A61M 5/42* | (2006.01) |
| *A61M 5/50* | (2006.01) |
| *A61N 1/05* | (2006.01) |
| *A61N 1/36* | (2006.01) |
| *A61B 90/00* | (2016.01) |
| *A61M 5/172* | (2006.01) |

(52) U.S. Cl.
CPC .............. *A61M 5/20* (2013.01); *A61M 5/427* (2013.01); *A61M 5/5086* (2013.01); *A61N 1/0502* (2013.01); *A61N 1/0551* (2013.01); *A61N 1/3605* (2013.01); *A61N 1/36017* (2013.01); *A61B 2090/0807* (2016.02); *A61B 2090/366* (2016.02); *A61M 2005/1726* (2013.01); *A61M 2205/13* (2013.01); *A61M 2205/3344* (2013.01); *A61M 2205/52* (2013.01); *A61M 2205/581* (2013.01); *A61M 2205/582* (2013.01); *A61M 2205/583* (2013.01); *A61M 2205/587* (2013.01); *A61M 2210/1003* (2013.01); *A61M 2230/60* (2013.01); *A61N 1/36031* (2017.08)

(58) Field of Classification Search
CPC ...... A61M 2005/1587; A61M 2205/13; A61M 2205/3344; A61M 2205/52; A61M 2205/581; A61M 2205/582; A61M 2205/583; A61M 2205/587; A61M 19/00; A61B 5/4896; A61N 1/0502; A61N 1/0551; A61N 1/36017; A61N 1/3605
See application file for complete search history.

(56) References Cited

U.S. PATENT DOCUMENTS

| | | | |
|---|---|---|---|
| 4,403,988 A | | 9/1983 | Binard |
| 4,518,383 A | | 5/1985 | Evans |
| 4,624,659 A | | 11/1986 | Goldberg |
| 4,679,567 A | | 7/1987 | Hanlon |
| 4,790,821 A | | 12/1988 | Stines |
| 4,801,293 A | | 1/1989 | Jackson |
| 4,893,630 A | | 1/1990 | Bray, Jr. |
| 4,988,337 A | | 1/1991 | Ito |
| 4,998,914 A | | 3/1991 | Wiest |
| 5,100,390 A | * | 3/1992 | Lubeck .............. A61B 17/3401 604/158 |
| 5,178,603 A | | 1/1993 | Prince |
| 5,197,895 A | | 3/1993 | Stupecky |
| 5,267,565 A | | 12/1993 | Beard |
| 5,269,762 A | | 12/1993 | Armbruster |
| 5,295,967 A | | 3/1994 | Rondelet et al. |
| D348,101 S | | 6/1994 | Poli |
| 5,378,231 A | | 1/1995 | Johnson |
| 5,405,269 A | | 4/1995 | Stupecky |
| D360,259 S | | 7/1995 | Ijiri |
| 5,520,650 A | | 5/1996 | Zadini |
| 5,611,778 A | | 3/1997 | Brinon |
| 5,660,567 A | | 8/1997 | Nierlich |
| 5,681,285 A | | 10/1997 | Ford |
| 5,690,618 A | | 11/1997 | Smith |
| D390,654 S | | 2/1998 | Alsberg |
| 5,727,553 A | | 3/1998 | Saad |
| 5,810,770 A | | 9/1998 | Chin |
| D409,148 S | | 5/1999 | Hirai |
| 5,902,273 A | | 5/1999 | Yang |
| 5,954,701 A | | 9/1999 | Matalon |
| 6,022,337 A | | 2/2000 | Herbst |
| 6,024,576 A | | 2/2000 | Bevirt |
| 6,120,457 A | | 9/2000 | Coombes |
| 6,126,610 A | | 10/2000 | Rich |
| 6,159,161 A | | 12/2000 | Hodosh |
| D436,927 S | | 1/2001 | Hogan |
| 6,200,289 B1 | | 3/2001 | Hochman et al. |
| 6,468,241 B1 | | 10/2002 | Gelfand |
| 6,569,147 B1 | | 5/2003 | Evans |
| 6,652,482 B2 | | 11/2003 | Hochman |
| 6,695,806 B2 | | 2/2004 | Gelfand |
| 6,705,990 B1 | | 3/2004 | Gallant |
| 6,716,192 B1 | | 4/2004 | Orosz, Jr. |
| 6,773,417 B2 | | 8/2004 | Fitzgibbons |
| 6,786,885 B2 | | 9/2004 | Hochman et al. |
| 6,866,648 B2 | | 3/2005 | Hadzic |
| 6,886,648 B1 | | 5/2005 | Hata et al. |
| 6,887,216 B2 | | 5/2005 | Hochman et al. |
| 6,942,637 B2 | | 9/2005 | Cartledge |
| 7,022,072 B2 | | 4/2006 | Fox |
| 7,198,602 B2 | | 4/2007 | Eide |
| 7,285,100 B2 | | 10/2007 | Lemaire |
| D556,910 S | | 12/2007 | Reihanifam |
| 7,335,162 B2 | | 2/2008 | Eide |
| 7,364,570 B2 | | 4/2008 | Gerondale |
| 7,395,214 B2 | | 7/2008 | Shillingburg |
| 7,449,008 B2 | | 11/2008 | Hochman |
| D600,644 S | | 9/2009 | Leung |
| 7,604,602 B2 | | 10/2009 | Roteliuk |
| 7,618,409 B2 | | 11/2009 | Hochman |
| 7,635,338 B2 | | 12/2009 | Eide |
| 7,641,637 B2 | | 1/2010 | Gerondale |
| 7,727,224 B2 | | 6/2010 | Hadzic |
| 7,775,985 B2 | | 8/2010 | Eide |
| D630,727 S | | 1/2011 | Wittwer |
| 7,896,833 B2 | | 3/2011 | Hochman |
| 7,922,689 B2 | | 4/2011 | Lechner |
| D642,984 S | | 8/2011 | Arai |
| 8,002,736 B2 | | 8/2011 | Patrick |
| 8,016,763 B2 | | 9/2011 | Eide |
| 8,079,976 B2 | | 11/2011 | Patrick et al. |
| 8,137,312 B2 | | 3/2012 | Sundar et al. |
| 8,142,414 B2 | | 3/2012 | Patrick |
| 8,197,443 B2 | | 6/2012 | Sundar et al. |
| 8,256,984 B2 | | 9/2012 | Fathallah |
| 8,262,584 B2 | | 9/2012 | Eide |
| D669,096 S | | 10/2012 | Katsura |
| D669,165 S | | 10/2012 | Estes |
| 8,282,565 B2 | | 10/2012 | Mahapatra |
| 8,308,654 B2 | | 11/2012 | Eide |
| 8,398,564 B2 | | 3/2013 | Eide |
| D679,379 S | | 4/2013 | Katsura |
| 8,444,592 B2 | | 5/2013 | Williams |
| 8,480,630 B2 | | 7/2013 | Mudd |
| D687,536 S | | 8/2013 | Shafer |
| 8,545,440 B2 | | 10/2013 | Patrick |
| 8,562,600 B2 | | 10/2013 | Kirkpatrick |
| 8,684,947 B2 | | 4/2014 | Eide |
| 8,764,668 B2 | | 7/2014 | Roteliuk |

(56) References Cited

U.S. PATENT DOCUMENTS

| | | |
|---|---|---|
| 8,814,807 B2 | 8/2014 | Hulvershorn |
| 8,896,324 B2 | 11/2014 | Kroh |
| 8,926,525 B2 | 1/2015 | Hulvershorn |
| 8,992,481 B2 | 3/2015 | Mudd |
| 8,998,841 B2 | 4/2015 | Shen |
| D730,514 S | 5/2015 | Havron |
| 9,044,542 B2 | 6/2015 | Patrick |
| D734,475 S | 7/2015 | Ross |
| D736,370 S | 8/2015 | Bodwell |
| D741,811 S | 10/2015 | Solomon |
| 9,199,044 B2 | 12/2015 | Bangera |
| 9,205,204 B2 | 12/2015 | Bangera |
| 9,358,038 B2 | 6/2016 | Hulvershorn |
| 9,358,350 B2 | 6/2016 | Bangera |
| D760,888 S | 7/2016 | Friedrich |
| D765,832 S | 9/2016 | Solomon |
| 9,443,446 B2 | 9/2016 | Rios |
| 9,452,261 B2 | 9/2016 | Alon |
| 9,468,396 B2 | 10/2016 | Mahapatra |
| 9,504,790 B1 | 11/2016 | Hochman |
| 9,603,537 B2 | 3/2017 | Lechner |
| 9,642,534 B2 | 5/2017 | Mahapatra |
| 9,655,528 B2 | 5/2017 | Zhu |
| D801,519 S | 10/2017 | Sloss |
| D803,386 S | 11/2017 | Sloss |
| D803,387 S | 11/2017 | Kerwin |
| 9,888,881 B2 | 2/2018 | Hulvershorn |
| 9,901,679 B2 | 2/2018 | Shen |
| 9,956,341 B2 | 5/2018 | Hockman |
| 10,004,450 B2 | 6/2018 | Moskowitz |
| 10,117,673 B2 | 11/2018 | Luo |
| 10,220,180 B2 | 3/2019 | Hochman |
| 1,038,361 A1 | 8/2019 | Moskovvitz |
| D859,634 S | 9/2019 | Hochman et al. |
| 10,406,285 B2 | 9/2019 | Anand |
| 1,046,383 A1 | 11/2019 | Hulvershorn |
| 1,060,295 A1 | 3/2020 | Silverstein |
| 2002/0016567 A1 | 2/2002 | Hochman |
| 2002/0016569 A1 | 2/2002 | Critchlow |
| 2002/0022807 A1 | 2/2002 | Duchon |
| 2002/0143294 A1 | 10/2002 | Duchon |
| 2003/0014006 A1 | 1/2003 | Alexandre |
| 2004/0035743 A1 | 2/2004 | Tighe |
| 2004/0149282 A1 | 8/2004 | Hickle |
| 2004/0215080 A1 | 10/2004 | Lechner |
| 2005/0004513 A1 | 1/2005 | Beyerlein |
| 2005/0004514 A1 | 1/2005 | Hochman |
| 2005/0096593 A1 | 5/2005 | Pope |
| 2006/0122555 A1* | 6/2006 | Hochman ............ A61M 5/1456 604/67 |
| 2006/0247657 A1 | 11/2006 | Trieu |
| 2007/0038143 A1 | 2/2007 | Christensen |
| 2007/0197922 A1 | 8/2007 | Bradley |
| 2008/0058702 A1 | 3/2008 | Arndt et al. |
| 2008/0103408 A1 | 5/2008 | Denton |
| 2008/0281265 A1 | 11/2008 | Hochman |
| 2009/0131832 A1 | 5/2009 | Sacristan Rock |
| 2009/0149911 A1 | 6/2009 | Dacey, Jr. et al. |
| 2009/0149912 A1 | 6/2009 | Dacey, Jr. et al. |
| 2009/0171191 A1 | 7/2009 | Patrick |
| 2009/0210029 A1 | 8/2009 | Tsui |
| 2009/0221914 A1 | 9/2009 | Barrett |
| 2009/0326482 A1 | 12/2009 | Hochman |
| 2010/0022918 A1 | 1/2010 | Fujie |
| 2010/0030102 A1 | 2/2010 | Poston |
| 2010/0049270 A1 | 2/2010 | Pastore |
| 2010/0056932 A1 | 3/2010 | Roteliuk |
| 2010/0179488 A1 | 7/2010 | Spiegel |
| 2010/0274191 A1 | 10/2010 | Ting |
| 2011/0021905 A1 | 1/2011 | Patrick |
| 2011/0046477 A1 | 2/2011 | Hulvershorn |
| 2011/0054353 A1 | 3/2011 | Hulvershorn |
| 2011/0060229 A1 | 3/2011 | Hulvershorn |
| 2011/0087166 A1 | 4/2011 | Davis |
| 2011/0112511 A1 | 5/2011 | Singer |
| 2011/0120566 A1 | 5/2011 | Ohmi et al. |
| 2011/0190596 A1 | 8/2011 | Hacker |
| 2011/0270179 A1 | 11/2011 | Ouyang |
| 2011/0288481 A1 | 11/2011 | Mudd |
| 2011/0298628 A1 | 12/2011 | Vad |
| 2011/0301500 A1 | 12/2011 | Maguire et al. |
| 2012/0022407 A1* | 1/2012 | Lechner ............... A61B 5/032 600/587 |
| 2012/0083760 A1 | 4/2012 | Ledford |
| 2012/0101410 A1 | 4/2012 | Lechner |
| 2012/0232389 A1 | 9/2012 | Guzman |
| 2012/0259237 A1 | 10/2012 | Axelrod |
| 2012/0289819 A1 | 11/2012 | Snow |
| 2012/0296176 A1 | 11/2012 | Herbst |
| 2013/0041258 A1 | 2/2013 | Patrick |
| 2013/0053851 A1 | 2/2013 | Schmitz et al. |
| 2013/0131633 A1 | 5/2013 | Mudd |
| 2013/0261533 A1 | 10/2013 | Norkunas |
| 2014/0012226 A1 | 1/2014 | Hochman |
| 2014/0066891 A1 | 3/2014 | Burns |
| 2014/0121636 A1 | 5/2014 | Boyden |
| 2014/0121637 A1 | 5/2014 | Boyden |
| 2014/0207050 A1 | 7/2014 | Gonzalez et al. |
| 2014/0221965 A1 | 8/2014 | Regittnig |
| 2014/0316268 A1 | 10/2014 | Kafiluddi et al. |
| 2014/0343406 A1 | 11/2014 | Damjanovic |
| 2015/0150519 A1 | 6/2015 | Glenn |
| 2015/0283365 A1 | 10/2015 | Dacey, Jr. et al. |
| 2015/0374929 A1 | 12/2015 | Hyde |
| 2016/0135712 A1 | 5/2016 | Holochwost |
| 2016/0136363 A1 | 5/2016 | McClellan |
| 2016/0228633 A1 | 8/2016 | Welsch |
| 2017/0106142 A1 | 4/2017 | Hochman |
| 2018/0064870 A1 | 3/2018 | Hochman |
| 2018/0087517 A1 | 3/2018 | Glenn |
| 2018/0116551 A1 | 5/2018 | Newman |
| 2018/0228968 A1 | 8/2018 | Hochman |

FOREIGN PATENT DOCUMENTS

| | | |
|---|---|---|
| EP | 0538259 | 4/1993 |
| FR | 2628625 | 9/1989 |
| HU | P8806113 | 10/1990 |
| HU | P0204296 | 3/2003 |
| JP | 5042218 | 2/1993 |
| JP | 6007440 | 1/1994 |
| JP | 6142114 | 5/1994 |
| WO | 1996005768 | 2/1996 |
| WO | 9725081 | 7/1997 |
| WO | 03000146 | 1/2003 |
| WO | 2010071416 | 6/2010 |
| WO | 2017/066732 | 4/2017 |
| WO | 2018152225 | 8/2018 |
| WO | 2018204668 | 11/2018 |

OTHER PUBLICATIONS

Cohen et al., "Functional deficits after intraneural injection during interscalene block", Regional Anesthesia and Pain Medicine, vol. 35, No. 4, Jul.-Aug. 2010, pp. 397-399.

Reiss et al., "Nerve injury complicating ultrasound/electrostimulation-guided supraclavicular brachial plexus block", Regional Anesthesia and Pain Medicine, vol. 35, No. 4, Jul.-Aug. 2010, pp. 400-401.

Lupu et al., "Nerve expansion seen on ultrasound predicts histologic but not functional nerve injury after intraneural injection in pigs", Regional Anesthesia and Pain Medicine, vol. 35, No. 2, Mar.-Apr. 2010, pp. 132-139.

Steinfeldt et al., "Histological consequences of needle-nerve contact following nerve stimulation in a pig model", Anesthesiology Research and Practice, vol. 2011, Feb. 2011, 9 pages.

Steinfeldt et al., "Forced needle advancement during needle-nerve contact in a porcine model: Histological outcome", Anesthesia & Analgesia, vol. 113, No. 2, Aug. 2011, pp. 417-420.

Sites et al., "Characterizing novice behavior associated with learning ultrasound-guided peripheral regional anesthesia", Regional Anesthesia and Pain Medicine, vol. 32, No. 2, Mar.-Apr. 2007, pp. 107-115.

(56) References Cited

OTHER PUBLICATIONS

Sites et al., "Incidence of local anesthetic systemic toxicity and postoperative neurologic symptoms associated with 12,668 ultrasound-guided nerve blocks", Regional Anesthesia and Pain Medicine, vol. 37, No. 5, Sep.-Oct. 2012, pp. 478-482.
Liu et al., "Incidence of unintentional intraneural injection and postoperative neurological complications with ultrasound-guided interscalene and supraclavicular nerve blocks", Anaesthesia vol. 66, 2011, pp. 168-174.
Abstract of: Bilbao et al., "Neurological complications associated with ultrasound-guided interscalene and supraclavicular block in elective surgery of the shoulder and arm. Prospective observational study in a university hospital", Rev Esp Anestesiol Reanim, vol. 60, No. 7, Aug.-Sep. 2013, pp. 384-391.
Widmer et al., "Incidence and severity of complications due to femoral nerve blocks performed for knee surgery", The Knee, Nov. 2012, 5 pages.
Hadzic et al., "Combination of intraneural injection and high injection pressure leads to fascicular injury and neurologic deficits in dogs", Regional Anesthesia and Pain Medicine, vol. 29 No. 5 Sep.-Oct. 2004, pp. 417-423.
Kapur et al., "Neurologic and histologic outcome after intraneural injections of lidocaine in canine sciatic nerves", Acta Anaesthesiologica Scandinavica, vol. 51, 2007, pp. 101-107.
International Search Report issued in International Patent Application No. PCT/US16/57264 dated Mar. 22, 2017.
International Preliminary Report on Patentability issued in International Patent Application No. PCT/US16/57264 dated Apr. 17, 2018.
Usubiaga et al., "Epidural Pressure and Its Relation to Spread of Anesthetic Solutions in Epidural Space", Anesthesia and Analgesia, vol. 46, No. 4, pp. 440-446, 1967.
Husemeyer et al., "Lumbar Extradural Injection Pressures in Pregnant Women", British Journal of Anaesthesia, 52, pp. 55-59, 1980.
Paul et al., "Extradural Pressure Following the Injection of Two Volumes of Bupivacaine", British Journal of Anaesthesia, 62, pp. 368-372, 1989.
Hirabayashi et al., "Effect of Extradural Compliance and Resistance on Spread of Extradural Analgesia", British Journal of Anaesthesia, 65, pp. 508-513, 1990.
Abstract of: Vas, "A study of epidural pressures in infants", Pediatric Anaesthesia, 11(5), pp. 575-583, 2001.
Lechner et al., "Clinical results with a new acoustic device to identify the epidural space", Anesthesia, 57, pp. 768-772, 2002.
International Preliminary Report on Patentability for PCT/US2013/045142 Filed on Jun. 11, 2013.
Ghelber et al., "Identification of the Epidural Space Using Pressure Measurement . . . ", Regional Anesthesia and Pain Medicine, vol. 33, No. 4, Jul.-Aug. 2008, pp. 346-352.
Official Action issued in U.S. Appl. No. 11/208,400 dated May 29, 2008, 10 pages.
Iff et al., "The Use of an Acoustic Device to Identify the Epidural Space in Cattle", The Veterinary Journal, 187 (2011) pp. 267-268.
Iff, Isabelle, et al., "The use of an acoustic device to identify the extradural space in standing horses", Veterinary Anaesthesia and Analgesia, 2010, 37, 57-62.
Lechner et al., "Clinical Results with the Acoustic Puncture Assist Device, a New Acoustic Device to Identify the Epidural Space", Anesthesia Analgesia, (2003) pp. 1183-1187.
Lechner et al., "Thoracic Epidural Puncture Guided by an Acoustic Signal: Clinical Results", European Journal of Anesthesiology, 21 (2004) pp. 694-699.
Lechner, T.J.M. et al., "The use of a sound-enabled device to measure pressure during insertion of an epidural catheter in women in labour", Anaesthesia, 2011, 66, pp. 568-573.
Tsui et al., "Reduced Injection Pressures Using a Compressed Air Injection . . . ", Regional Anesthesia and Pain Medicine, vol. 33, No. 2, Mar.-Apr. 2008, pp. 168-173.
Extended European Search Report issued in EP Application No. 13813314.5 dated Feb. 18, 2016.

Examination Report issued in Australian Patent Application No. 2013287174 dated Oct. 26, 2016.
International Search Report and Written Opinion issued in PCT/US16/63861 dated Mar. 6, 2017.
Jonathan Dillon, "Embedded storage in disposable medical items"; Article posted on Aug. 1, 2011; https://www.electronicproducts.com/Digital_ICs/Memory/Embedded_storage_in_disposable_medical_items.aspx.
"Medical Device Sanity"; http://mdgoo.blogspot.com/2014/12/another-medical-device-supplier-with.html; published prior to Oct. 27, 2017.
Maxim Integrated Product Specification for DS28EC20 20Kb 1-Wire EEPROM; published prior to Oct. 27, 2017.
International Preliminary Report on Patentability issued in International Application No. PCT/US13/45142 dated Jan. 15, 2015.
Al-Aamri, et al., "Reliability of Pressure Waveform Analysis to Determine Correct Epidural Needle Placement in Labouring Women", Anaesthesia 2017, 72, pp. 840-844.
Cohen et al, "Epidural Block for Obstetrics: Comparison of Bolus Injection of Local Anesthetic with Gravity Flow Technique", Journal of Clinical Anesthesia, 9, 1997, pp. 623-528.
Cohen et al, "Extradural Block in Obstetric Patients: Review of Experience with Gravity Administration", Acta Anaesthesiologica Scandinavica, 35, 1991, pp. 676-679.
Dawkins, "The identification of the epidural space" Anaesthesia, vol. 18, No. 1, Jan. 1963, pp. 66-77.
McKendry et al., "Pressure Waveforms to Assess Epidural Placement: Is There a Role on Delivery Suite?", Anaesthesia, 72, 2017, pp. 815-820.
Ghia, et al, "Confirmation of Location of Epidural Catheters by Epidural Pressure Waveform and Computed Tomography Cathetergram", Regional Anesthesia and Pain Medicine, vol. 26, No. 4 Jul.-Aug. 2001, pp. 337-341.
Gong et al, "Pressure Waveform-Guided Epidural Catheter Placement in Comparison to the Loss-of-Resistance Conventional Method", Journal of Clinical Anesthesia, 26 (2014) pp. 395-401.
Hong et al, "Analysis of Epidural Waveform for Cervical Epidural Steroid Injections Confirmed with Fluoroscopy", An.md-journal.com, Hong and Jung Medicine (2018) 97:13, 4 pages.
Lennox et al, "A Pulsatile Pressure Waveform Is a Sensitive Marker for Confirming the Location of the Thoracic Epidural Space", Journal of Cardiothoracic and Vascular Anesthesia, vol. 20, No. 5 Oct. 2006, pp. 659-663.
Leurcharusmee et al, "Reliability of Waveform Analysis as an Adjunct to Loss of Resistance for Thoracic Epidural Blocks", Regional Anesthesia and Pain Medicine, vol. 40, No. 6, Nov.-Dec. 2015, pp. 694-697.
Suwa et al, "Pressure-Guided Method for Identification of the Epidural Space in Children", Anesthesiology, vol. 89, No. 2, Aug. 1998, pp. 546-548.
Hsu et al, "The Frequency and Magnitude of Cerebrospinal Fluid Pulsations Influence Intrathecal Drug Distribution: Key Factors for Interpatient Variability", www.anesthesia-analgesia.org, vol. 115, No. 2, Aug. 2012, pp. 386-394.
Wagshul et al, "The pulsating brain: A review of experimental and clinical studies of intracranial pulsatility", http://www.fluidsbarrierscns.com/content/8/1/5, 2011, 8:5, 23 pages.
Hettiarachchi et al, "The Effect of Pulsatile Flow on Intrathecal Drug Delivery in the Spinal Canal", Annals of Biomedical Engineering, vol. 39, No. 10, Oct. 2011, pp. 2592-2602.
Hilber et al, "A systematic review of the diagnostic accuracy of epidural wave form analysis to identify the epidural space in surgical and labor patients", http://www.minervamedica.it, Minerva Anestesiologica, Apr. 2019, 85(4), pp. 393-400.
Iff et al., "The Use of an Acoustic Device to Identify the Extradural Space in Standing Horses", Veterinary Anesthesia and Analgesia, 37 (2010) pp. 57-62.
Hungarian Novelty Report for Application No. P 04 00176.
NL Search Report, NL 2002708, dated Oct. 9, 2009.
PCT International Prelminary Report on Patentability, PCT/NL2010/000061, dated Oct. 4, 2011.
PCT International Search Report, PCT/NL2010/000061, dated Aug. 23, 2010.

(56) References Cited

OTHER PUBLICATIONS

International Search Report and Written Opinion issued in International Application No. PCT/US18/31096 dated Sep. 10, 2018.
Ross et al., "Pressures of Injection in a Cadaver Model of Peripheral Nerve Blockade", Journal of Anesthesia & Clinical Research, 2014, vol. 5, Issue 10, 4 pages.
Product brochure "PAJUNK: NerveGuard Automatic system for injection pressure limitation" (XS200192B) dated Jan. 2017, 4 pages.
https://www.dermaqueen.co.ki7, published prior to Feb. 15, 2017.
http://www.intranixtech.com/myoguide-system/, published prior to Feb. 15, 2017.
http://www.anteis.com/AestheticDermatology/injectionsystem.php, published prior to Feb. 15, 2017.
International Search Report & Written Opinion issued in International Application No. PCT/US13/45142 dated Sep. 10, 2013.
International Preliminary Report on Patentability issued in International Application No. PCT/US06/29091 dated Feb. 28, 2008.
Gadsden, et al., "High Opening Injection Pressure Is Associated With Needle-Nerve and Needle-Fascia Contact During Femoral Nerve Block", Regional Anesthesia and Pain Medicine, vol. 41, No. 1, Jan.-Feb. 2016, pp. 50-55.
Lacoste, " DSSS in a nutshell the Powerof Patterns at Play", Circuit Cellar, Apr. 2020, #357, pp. 62-67.
International Search Report & Written Opinion issued in International Application No. PCT/US20/29857 dated Jul. 21, 2020.

\* cited by examiner

APPARATUS FOR ASSISTING A USER IN ADVANCING A NEEDLE INTO A SUBJECT AT A SELECTED RATE

PRIORITY CLAIM

The present application is a U.S. National Stage of International Application No. PCT/US16/57264 filed Oct. 17, 2016, which is a continuation-in-part of U.S. patent application Ser. No. 15/062,685 filed on Mar. 7, 2016 and U.S. patent application Ser. No. 15/141,231 filed Apr. 28, 2016. The present application also claims priority to U.S. Provisional Patent Application No. 62/242,745 filed Oct. 16, 2015. The entire disclosure of each of the foregoing patent applications is hereby incorporated herein by reference.

FIELD OF THE INVENTION

The present invention relates generally to improvements to the delivery of drugs, particularly to systems for subcutaneous injection/aspiration into the body. More specifically, the invention provides a method and device to perform an injection that provides feedback for the medical practitioner during subcutaneous placement of a needle.

BACKGROUND OF THE INVENTION

In various medical procedures it is desirable to place a needle in a particular area to inject a medical solution, such as an anesthesia or analgesic. Two such examples are a regional anesthesia block of epidural tissue-space and a peripheral nerve block (PNB). For an epidural to achieve effective regional anesthesia and to block nerve transmission to the central nervous system an adequate volume of a local anesthetic solution must be deposited in close proximity to the spinal cord at a particular level of the vertebral column within the anatomic site known as the epidural "space." For a peripheral nerve block a target nerve is identified and a needle is placed in close proximity to deliver an anesthesia to the nerve. Each of these procedures have issues related to the relevant anatomy.

The epidural space is that part of the vertebral canal not occupied by the dura mater and its contents. It lies between the dura and the periosteum lining the inside of the vertebral canal. It extends from the foramen magnum to the sacral hiatus. The anterior and posterior nerve roots in their dural covering pass across the epidural space to unite in the intervertebral bodies, and the intravertebral discs. Laterally, the epidural space is bordered by the periosteum of the vertebral pedicles, and the intervertebral foramina. Posteriorly, the bordering structures are the periosteum of the anterior surface of the laminae, the articular processes and their connecting ligaments, the periosteum of the root of the spines, and the interlaminar spaces filled by the ligamentum flavum. The space contains venous plexuses and fatty tissue which is continuous with the fat in the paravertebral space.

The epidural fluid filled space (posterior epidural space) is a limited anatomic area with an irregular shape measuring in several square millimeters with respect to cross section of the vertebrae and spinal column. The fluid filled space is narrow and is associated closely with the dura of the spinal column with the ligamentum flavum closely adjacent. Therefore, during insertion of an epidural needle, it is desirable to know the when the tip of the epidural needle enters the fluid filled space after piercing the ligamentum flavum. If the needle continues to be inserted after the tip enters the fluid filled space, the needle may puncture the dura.

The clinician palpates the vertebral column at the appropriate level of the vertebral column between vertebrae. Local anesthesia is placed within the superficial tissues thereby locally anesthetizing the tissue. The dermis is then punctured using a Tuohy needle and the needle is advanced while the clinician simultaneously applies pressure on the plunger of the syringe. The pressure on the plunger will unintentionally result in an amount of fluid continuously exiting out of the needle within the tissues.

Unfortunately, if the epidural procedure is not performed properly or if one is distracted while performing this procedure the needle can be advanced beyond the intended target and cause damage to the spinal cord. It is known in that between 2-3% of all injections go beyond the intended target and penetrate the dura causing a needle to make direct contact to the spinal fluid space and in some instances direct contact to the spinal cord can occur leading to a life threatening situation. Therefore, precise and careful visual attention should be maintained throughout the procedure to monitor the precise location of the needle during the entire procedure of placing the needle into the epidural space.

Additionally, if the Tuohy needle moves once the epidural space has been located, either by removal of the syringe or inadvertent movement of the patient or doctor's hand, the needle can either be unknowingly moved outside the epidural tissue-space or at worst advanced into dura of the spinal cord producing what is termed a "wet-tap", which can have a dangerous long-term consequences to the patient. Even if the epidural space was initially properly located, if the needle further advances during the injection of the anesthetic solution it may deposit a bolus of anesthetic solution into the spinal cord resulting in transient or permanent nerve damage.

In addition to the above stated deficiencies, pressure monitoring can be affected by the forward movement of a needle within tissues during penetration of the tissues. As the needle is advanced into tissues a counter-active head-pressure is generated accordingly to Newton's third law of physics. A biasing counter force is created on the head-pressure of a fluid emitted from a needle tip as the needle is advanced through tissues. This counter force introduces inaccuracies in exit-pressure measurement particularly if pressure monitoring is conducted on a continuous and real-time basis during the advancement and injection of a drug into tissues. Non-uniform advancement movement of the needle into bodily the tissues produces pressure spikes and inaccuracies in the pressure measurements can lead to false-positive confirmation of a maximum exit-pressure.

Referring to FIG. 12, a description of the microanatomy of the peripheral nervous system is provided. The basic building block to both the central and peripheral nervous system is the single cell unit commonly known as is the axon. The brain and central nervous system are composed of millions of axons. Branching off the central nervous system of the brain stem and spinal cord is a collection of highly organized axons forming a network of sensory and motor pathways via the axons. This network of pathways is collectively known as the peripheral nervous system.

In the peripheral nervous system, each individual axon is surrounded by supporting connective tissue called the endoneurium. Contained within the endoneurium are small blood vessels (capillaries and venuoles) providing nutrients to these axons. Axons are collectively formed into highly organized, packed bundles that are surrounded by a thin but dense multi-layered connective tissue sheath that surrounds and forms a membrane structure called the perineurium. The perineurium provides a dense protective layer that is both a physical and chemical barrier, providing a degree of protection for the axons and endoneurium. This barrier is akin to the blood-brain barrier.

This discrete unit of the endoneurium and perineurium is called a peripheral nerve fascicle. When fascicles coalesce together they form fascicular bundles embedded in epineurium, which is a connective tissue sometimes referred to as inner epineurium. The multiple groups of fascicles are embedded in a non-uniform matrix of connective tissue (fibro-adipose tissue) and mid-size vessels that are loosely arranged together with an outer perimeter of dense connective tissue. The bundled fascicular structures collectively surrounded by this additional densely, more highly organized layer of fibrous tissue, houses the peripheral nerve contents and is known as the outer epineurium.

The outer epineurium connects the outer layer to the neighboring structures. A loose connective tissue fills the space between the nerve and the surrounding tissue in connection with the outer epineurium. There is thus an additional multi-layer boundary beyond the outer epineurium that runs along the entire trajectory of the nerve and is composed of an extraneural connective tissue known as the paraneurium. The paraneurium is a distinct multi-layer functional structure that enables the nerve to glide relative to other anatomic structures during muscular-skeletal movements.

To aid in locating a nerve branch, electrical stimulation was proposed in the year 1912. Electrical nerve stimulation was introduced from an understanding that nerve transmission is an electro-chemical response of excitation along the nerve (an axon). Introducing an electrical current stimulation to the body had the ability to elicit an indirect excitation of both the sensory and motor components of a nerve. This was found to provide a visual muscle contraction when the electrical stimulation was applied. Modulating the charge frequency and intensity lead to contraction and relaxation of muscle groups innervated by a nerve branch. This use of an indirect electrical charge to produce a nerve reaction to a specific nerve did not gain popularity because clinicians were unable to precisely control the various parameters of the current applied. The same deficiencies known when nerve stimulation was first introduced still exist today, including:

An inability to accurately modulate an applied electrical charge at a given distances to the surface of a nerve branch has made nerve stimulation limited in the identification of a specific nerve branch when using nerve stimulation as the primary means of nerve branch location. A variety of charge intensities are recommended at specific distances when approaching the nerve branch blindly ranging from an intensity of 2.0 mA to 0.2 mA. However, distance and intensity noted by a visual muscle twitch reaction does not correlate. Therefore, a reaction to a greater stimulation does not necessarily mean the needle is a greater distance to the intended nerve branch. And a reaction to a lower electric charge does not mean the needle is closer to the surface extraneural position and/or located within the nerve, i.e., achieved an intraneural location. In fact, there appears to be no consensus on the location of a needle (intraneural or extraneural) based on a reaction to an applied electrical charge irrespective of the intensity, frequency and duration applied to the nerve at a given distance.

A further deficiency of nerve stimulation technique is the inability to set the appropriate charge for a defined distance from the outer surface of the fascicle, i.e., Extra-Fascicular. It is more concerning if a high charge above 1.0 mA is utilized Intra-Fascicular, as it may cause a severe response by the patient or, even worse, result in irreversible damage from an excessive electrical charge applied directly on the axon. Hence there is an inability to determine what appropriate charge should be applied for a specific distance from the fascicle.

A further deficiency is that confounding variables make the use of nerve stimulation a non-specific technique. These are related to anatomic variations within a given patient as well as anatomic variation between different patients. The body is comprised of a variety of tissue types which include connective tissue of mineralized and non-mineralized tissues. These tissues are composed of water and collagen, adipose tissue (fat), muscle, fluids (blood), bone, cartilage, etc. Each of these tissues types provides a different resistance and/or capacitance to a charge when it is applied at a given distance to the intended target. The variables of tissue cannot be underestimated or anticipated. Hence current devices lack the ability to quantify a specific charge to a specific location. This has lead to an inability to produce predictable response to a given electrical charge when used as the primary means of determining location or proximity to a specific nerve.

In summary, the variables of charge intensity, frequency and tissue resistance to the electric charge have made it difficult to standardize a technique to enable location of a specific nerve branch.

SUMMARY OF THE INVENTION

In light of the shortcomings of the prior art, the present invention provides an injection system that improves the reliability and safety of injections particularly of those injections that are performed to identify fluid filled spaces contained within the body by narrow layers of fascia or connective tissue. By allowing information, particularly continuous pressure monitoring to be projected upon the surface of a patient at the location of needle entry, the operator can carefully and continuously monitor needle movement while obtaining critical injection parameters such as exit-pressure, flow-rate, warnings, exit-pressure threshold changes and any important information that was typically displayed elsewhere. This allows the operator to maintain visual focus at the site of the injection at all times.

Additionally, according to another aspect, the present invention provides an apparatus and method that can provide a mechanism for an operator to continuously guide the insertion of a needle while simultaneously receiving visual information projected upon the surface of the a patient at the site of the injection, thus enabling the operator to continuous maintain the view of the needle and the injection site to enable precise eye hand coordination to be maintained continuously. This information can be provided in a variety of formats from color changes, images, numbers, words and visual changes to these formats including intensity, blinking, coordinated illumination patterns, etc.

According to a further aspect, the present invention provides an infusion device that continuously monitors fluid pressure of the fluid being infused to the subject. The pressure resistance measure may then be converted into a visual signal on a continuous basis. The measurements are then presented to the medical professional so that the medical professional can determine or confirm whether the injection is being delivered to the correct tissue. In addition, the measurements are also recorded for later review and documentation of the clinical event. Upper limits of pressure as well as control of flow-rate can be pre-defined to ensure that excessive pressure and/or flow-rate are not used during this process.

According to a still further aspect, the present invention provides a method and apparatus for utilizing counter-head pressure when calculating the exit pressure. The counter-head pressure is related to the insertion rate of the needle. Therefore, the system includes a mechanism for controlling the insertion rate of the needle. In particular, the system may include markings on the needle and auditory or visual cues for prompting the appropriate insertion rate for the needle.

Additionally, another aspect of the present invention provides a hand-piece to which a marked needle is connected that is designed to house a small display, such as an LED light or display screen that will provide a blink or visual instruction and/or speaker and/or beeps or provides an audible tone that can be intermittent to enable the coordination of the defined forward movement to the provided visual or audible signal to the advancement of the needle based upon the markers on the surface of the needle as it penetrates the skin or other part of the body. The audible and visual cadence defines the rate of advancement of the needle so that it can be coordinated to forward movement to improve the accuracy of counter head-pressure produced and provided to the calculation of the real-time exit-pressure monitoring.

One aspect of the present invention provides a mechanism for distinguishing between intra-fascicular and extra-fascicular needle placement.

Another aspect of the current invention is a current charge that is transmitted via an ionic solution through a disposable syringe and tubing to the tip of the needle for the purpose of nerve stimulation.

A further aspect of the current invention is a system that provides a constant flow of fluid from the tip of the needle during the advancement of a needle movement through tissues when performing a peripheral nerve block to prevent the needle tip from entering the fascicle. The constant flow of fluid from a needle tip acts as a means to move or push dense structures away from the tip of a needle as it advances.

Yet another aspect of the current invention is a system that provides a defined rate or pace of forward movement to the needle within the tissues to prevent a biasing counter head-pressure force applied upon a needle as one is advancing said needle into and through the tissues while simultaneously and continuously measuring a pressure at tip of the needle.

Still another aspect of the current invention provides that when the needle is not being advanced the counter head-pressure will not be subtracted from the calculation of the exit-pressure. It is understood that the button or control on the hand-piece may also be activated to correspond with the forward movements in which the counter head-pressure is subtracted from the calculation of the head-pressure therefore providing a means to distinguish between when the needle is being advanced and when the needle remains stationary within the tissues.

The current invention also provides a hand-piece to which a marked needle is connected that is designed to house a small LED light or display screen and/or speaker that will blinks and/or beep in coordination to said rate to advance said needle. The hand-piece may possess input elements to control flow-rate, electrical current stimulation and communicate with the CPU of the drive unit. Additionally, the hand-piece may possess a vibratory chip or element to provide vibration of the hand-piece to communicate a command or signal from the CPU to the operator. This vibratory sensation can be discreet and represent a command warning or signal for the operator to respond to. The hand-piece may also include an output display to additional display information.

The present invention also provides an injection device for providing a peripheral nerve block that uses maximum back pressure range between 75 mm/Hg to 500 mm/Hg to trigger an electrical stimulation. An instantaneous discrete emission of a current may be provided when a specific pressure value is detected within the pressure range. This signal is to control an instantaneous discreet emission of a current at a specific pressure value within stated pressure range.

According to another aspect, the system uses a biasing head-pressure value that is set in a CPU that is determined and correlated to a rate (pace) of forward movement to the marked needle within the tissues. Biasing head-pressure value is calculated and is factored into the calculated head pressure value to eliminate pressure bias from the counter head-pressure value of a needle resulting from forward movement during simultaneously use of continuous flow and pressure monitoring.

According to a further aspect, an injection device is provided that provides a current between 0.15 mA to 2.0 mA. The current is provided in response to a detected exit-pressure value. Further, the electric charge is to be emitted as for a discreet period between 1.0 to 10.0 seconds. Simultaneously, when the electric charge is emitted a control signal is transmitted to the CPU to which a response is required. An example of a response to the control signal would be:

i) verification of muscle twitch.

ii) change to higher flow-rate to dispense drug.

A further aspect of the present invention is to have a first condition (specific exit-pressure value at a fixed-flow rate) and second condition (emitted current stimulation) requiring a response by the operator to set a third condition (positive/negative observation) to result in an output (instruction and warning signal).

Yet another aspect of the present invention is a device that provides a means to advance the needle within the tissues at an advancement rate between 2 and 20 mm/sec with constant flow of fluid at a defined flow-rate.

According to a still further aspect, the present invention provides a method and apparatus for utilizing counter-head pressure when calculating the exit pressure. The counter-head pressure is related to the insertion rate of the needle. Therefore, the system includes a mechanism for controlling the insertion rate of the needle. In particular, the system may include markings on the needle and auditory or visual cues for prompting the appropriate insertion rate for the needle.

Additionally, another aspect of the present invention provides a hand-piece to which a marked needle is connected that is designed to house a small display, such as an LED light or display screen that will provide a blink or visual instruction and/or speaker and/or beeps or provides an audible tone that can be intermittent to enable the coordination of the defined forward movement to the provided visual or audible signal to the advancement of the needle based upon the markers on the surface of the needle as it penetrates the skin or other part of the body. The audible and visual cadence defines the rate of advancement of the needle so that it can be coordinated to forward movement to improve the accuracy of counter head-pressure produced and provided to the calculation of the real-time exit-pressure monitoring.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 1:
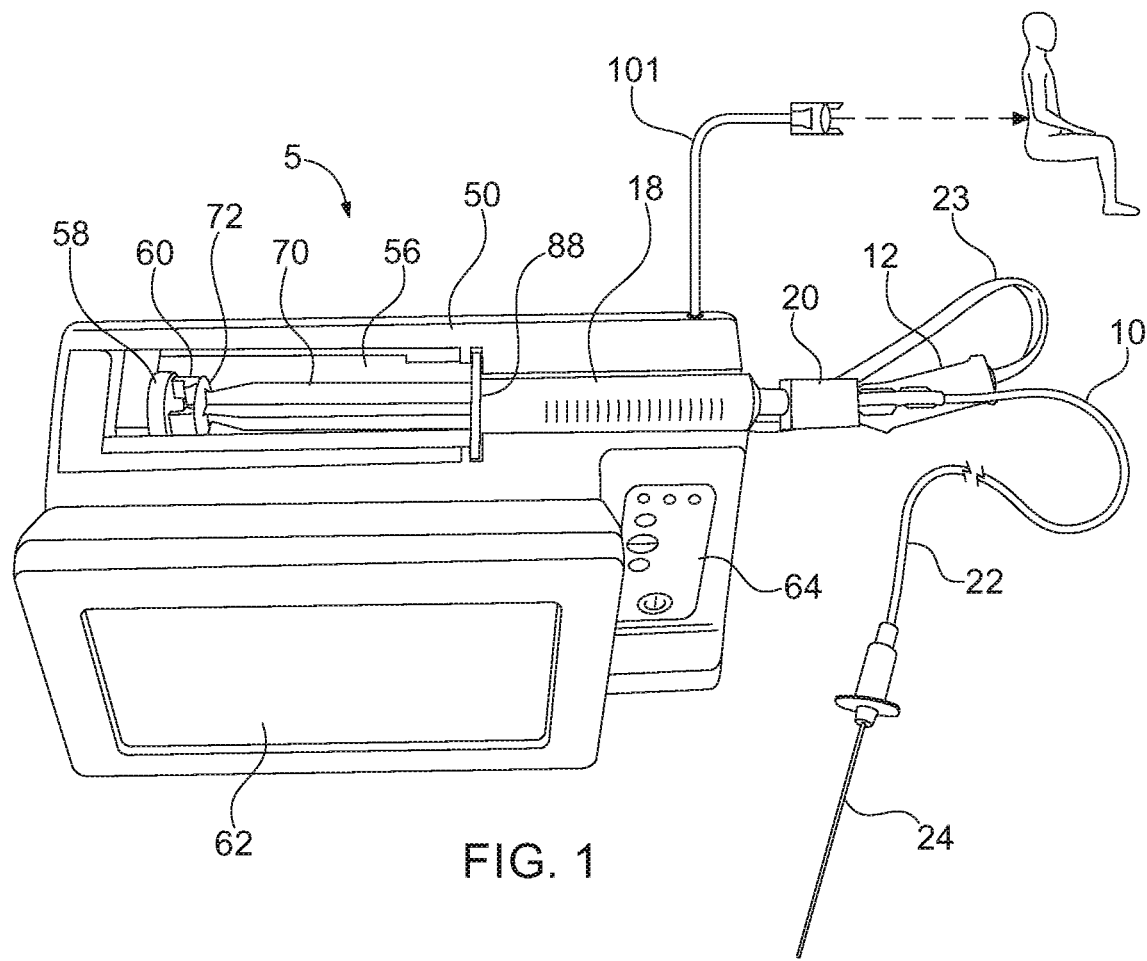
FIG. 1 is a perspective view a drug delivery system.
Figure 2:
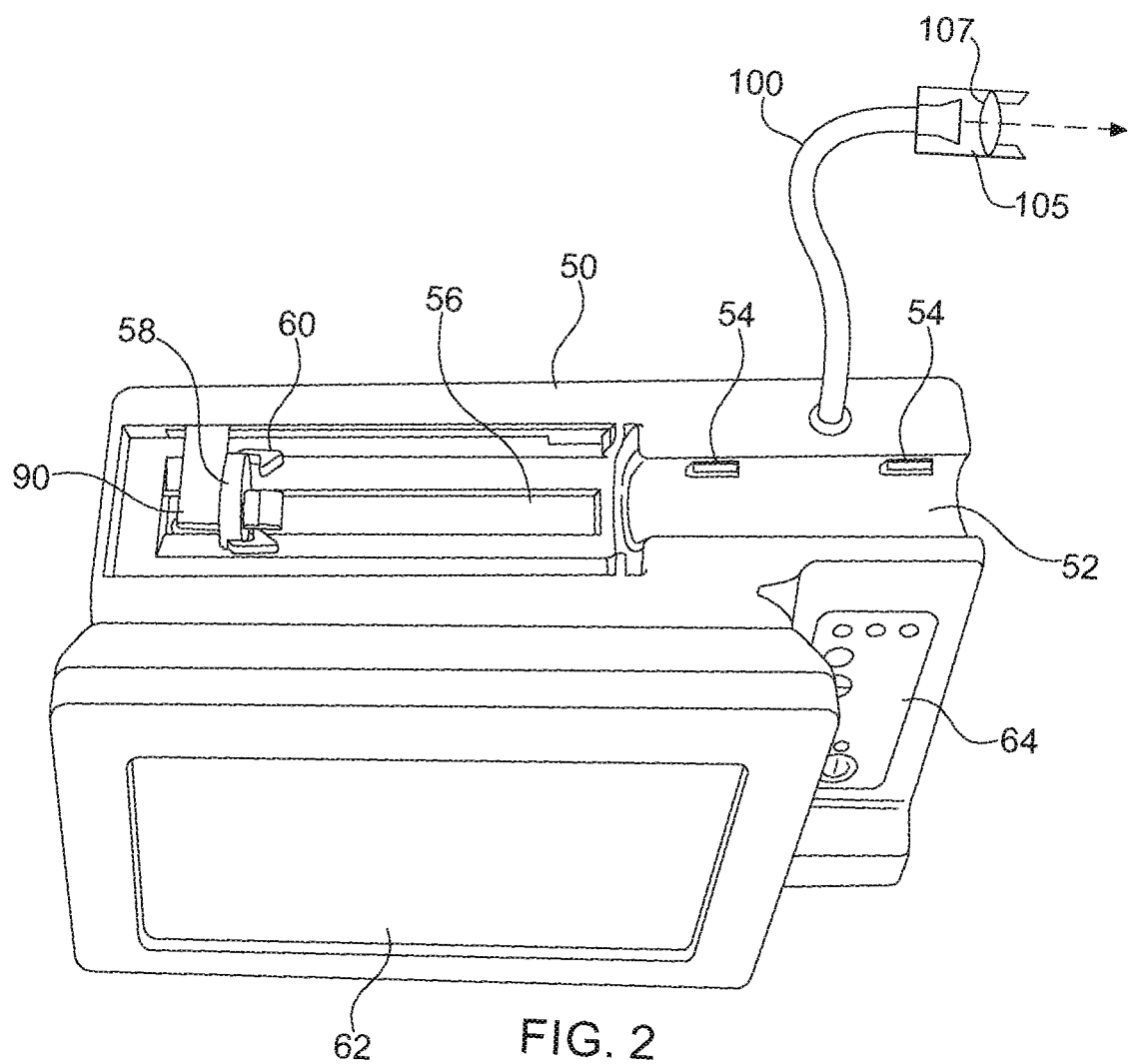
FIG. 2 is a perspective view of the drug delivery system illustrated in FIG. 1, shown with a injection assembly removed.
Figure 3:
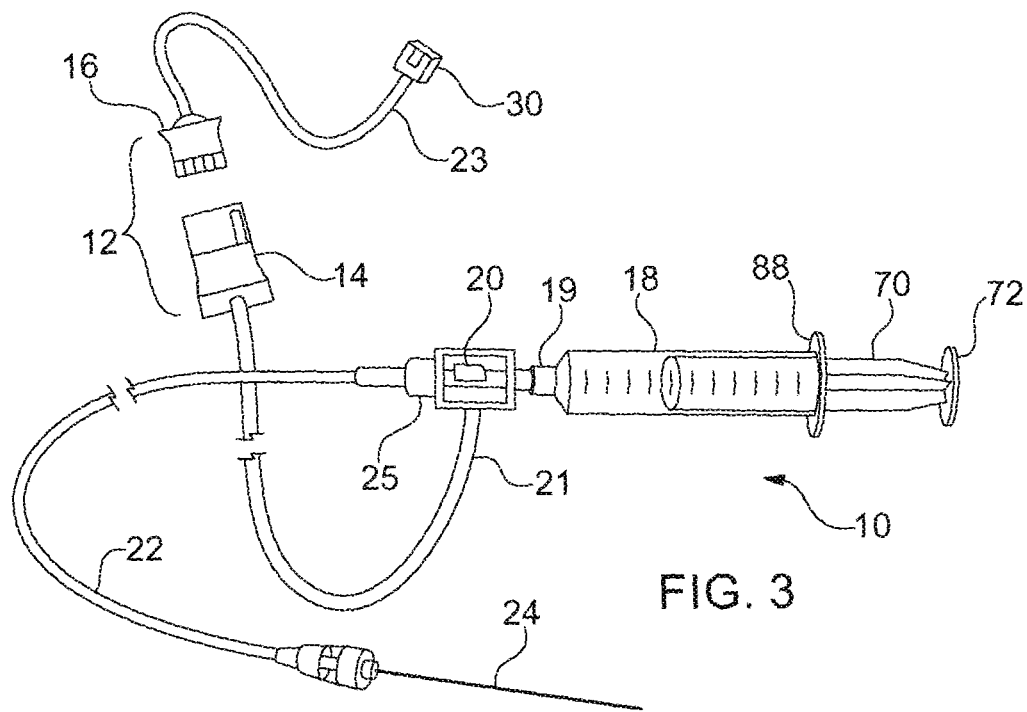
FIG. 3 is side view of an injection assembly of the drug delivery system illustrated in FIG. 1.

Referring now to the drawings, in general and to FIGS. 1-3 specifically, a drug infusion system is designated generally 5. The system 5 includes a disposable injection assembly 10 and a computer-controlled drug delivery instrument 50, referred to as a drive unit. The injection assembly 10 includes an insertion needle 24 configured for insertion into a mammalian subject. The injection assembly 10 is connected with the drive unit 50, which controls the flow of fluid to the injection assembly during use. The system 5 also includes one or more output mechanisms that provide data to the medical professional during a procedure to assist in proper placement of the needle in the subject.

The system 5 is operable to determine the location of fluid-filled tissue such as the epidural space, intra-articular space, globe of the eye, cysts, vessels and other fluid-filled spaces of the body. The system is also operable to deliver therapeutic medication to such fluid-filled tissue. The medication may include, but is not limited to local anesthetic solutions, such as, cortico-steroids, hydroxyapatite, joint replenishment drugs, sclerosing agents and other drugs that are typically injected into a fluid-filled tissue space for therapeutic purposes.

Injected fluid disperses through tissue at different rates. As a result, the fluid pressure varies. Therefore, this fluid pressure (or an internal pressure related to the resistance pressure of a tissue) is indicative of, and may be used to identify several types of tissues.

The system 5 enables a practitioner to accurately identify fluid-filled tissue space while limiting the placement of drugs into non-targeted tissues. This is performed for both diagnostic and therapeutic procedures. The system 5 utilizes the pressure of a fluid from a needle or catheter following placement of the needle/catheter within the tissue in order to identify the accuracy of placement and to monitor the placement during an injection or aspiration.

Specifically, the system 5 includes one or more output mechanisms for providing visual feedback of the detected fluid pressure in the insertion needle. The operator uses the visual feedback as guidance during the placement of the insertion needle. As shown in FIGS. 1&2, the first output mechanism may be a video display screen, such as an LCD display for displaying data to aid the operator. Additionally, a second output mechanism may also be provided. For example, the second output mechanism may be a light emitting element configured to provide an output signal during a procedure that is in the field of view of the operator. For instance, the second output mechanism may be a light emitting element operable to project a beam of light onto the patient adjacent the site where the needle is inserted into the patient.

Injection Assembly

Figure 4:
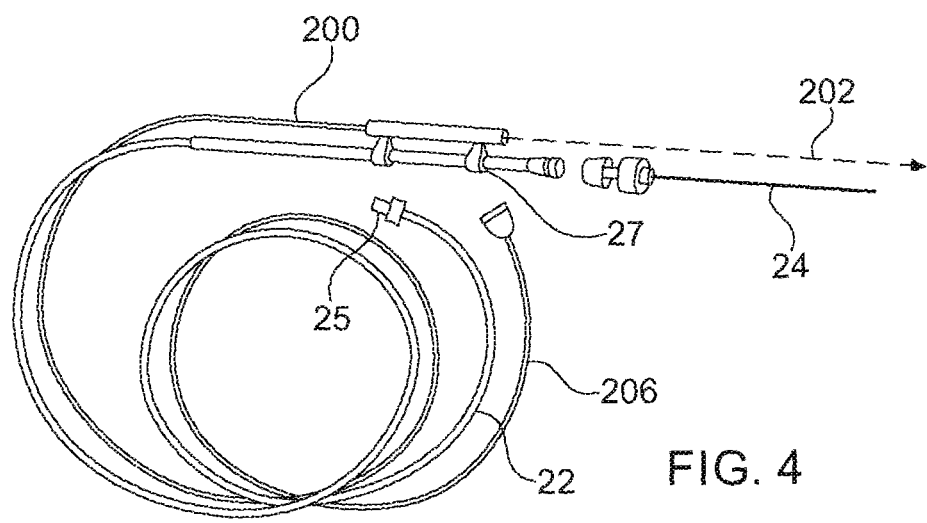
FIG. 4 is a fragmentary side view of an alternate injection assembly of the drug delivery system illustrated in FIG. 1.

Referring to FIGS. 3-4, the system 5 includes a disposables injection assembly 10 that includes a syringe 18 and an elongated length of flexible tubing 22 having a first end connected with the syringe and an insertion needle 24 connected with the second end. In this way, fluid from the syringe can be expelled through the tubing 22 and into the needle 24. The injection assembly 10 also includes a pressure sensor for detecting fluid pressure in the injection assembly. The pressure sensor may be disposed in one of several locations to measure a pressure that correlates with the fluid pressure at the tip of the needle 24. In the present instance, the pressure sensor 20 is an inline fluid pressure sensor attached to the syringe 18 between the syringe and the tubing 22. In this way, the pressure sensor 20 senses the fluid pressure as the fluid exits the syringe and enters the tubing 22 to which the insertion needle 24 is connected.

The computer-controlled drug delivery system 50 of the system, illustrated in FIGS. 1-2, provides numerous benefits to patients by providing an accurate injection. An output cable 21 connects the pressure sensor 20 with the drug delivery system 50 so that the drug delivery system can vary the flow of fluid from the syringe in response to the data from the pressure sensor 20. In this way, the drug delivery system 50 provides precise and safe administration of drugs for a variety of application such as epidurals, inter-articular and other subcutaneous injections. Connection 12 is connected with a second cable 23 and a jack 30 that is plugged into the instrument 50. The pressure-transducer 20 is connected inline between the forward end 19 of the cylinder of syringe 18, and the first end 25 of tubing 22. One exemplary connection is a Luer connection for connecting the pressure-transducer 20 to the tip of the syringe. The connection may be fixed by a threaded connection and/or an irreversible threaded connection, such as a LuerLok. Alternatively, in the present instance, the pressure transducer 20 is permanently fixed to the syringe by plastic welding or chemical binding, such as adhesive. In this way, the instantaneous, actual fluid pressure in the drug delivery line 22 is sensed and used by the instrument, which provides a close approximation to the actual, instantaneous fluid pressure at the point or tip of the needle 24, and therefore, at the location in the patient's body where the tip is located. The electronic pressure-transducer 20 provides pressure data via the electronic data cables 21, 23 that are connected directly to the central unit 50 to collect the pressure measurements.

The disposable injection assembly 10 is provided as a single use disposable set in which all components are connected and in the present instance, the connection is permanent. For example, the components of the injection assembly may be welded or bonded together by glue, epoxy or other adhesive, i.e. the syringe 18 is permanently bonded to the tubing-set 22 with electronic pressure sensor or transducer 20 permanently bonded there between. This disposables assembly 10 is used and discarded as a unit. It is further connected to the drive unit 50 by a second connector 16 that can key into connector 14 to ensure that only authorized disposables assemblies 10 are used and that they are only used once.

The electronic pressure transducer 20 can be any of various pressure sensors. One type of exemplary sensor is a piezoelectric pressure sensor, such as sensors available from Merit Medical Systems, Inc. such as the Meritrans® Pressure Transducer item MER212.

In the preferred embodiment the permanent attachment of the needle may be optional so that a practitioner may selection a preferred needle for a particular purpose. The components are assembled individually or as in the preferred embodiment they are glued (i.e. bonded) together and provided as a single disposable set-up ensuring that the proper disposable components were selected.

The preferred embodiment is a bonded disposable setup. It is anticipated that a variety of configurations could be used in conjunction with the instrument 50. These consist of different size components, i.e. needle, syringe, tubing-set and pressure transducers. The system may incorporate an identification connector that uniquely identifies the details of each injection assembly (e.g. needle size, tube length etc.) The integration of an identification connector confirms and identifies the disposable set-up to be used. This represents a verification to the system that promotes use of appropriate components and/or drugs. It is anticipated that a pre-filled syringe 18 with a drug could be supplied with the injection assembly 10, or the syringe can be supplied empty so that it can be filled onsite with a desired drug, saline or other fluid. For pre-filled syringes 18, the identification connector 12 (in a microchip) contains the information related to the drug contained within the syringe.

FIG. 4 illustrates parts of an alternate disposable injection assembly. This embodiment includes an axially elongated rigid, plastic, sterile handle 27 fixed to the second end of the tubing 22 and having a connector, such as a male Luer lock that is to be detachably connected to a needle 24 of choice for a particular type of injection into a selected anatomic site. The elongated handle 27 of this embodiment increases manual control and dexterity in placing the needle, in particular because of rotational control. This is particularly helpful for IA-injections (i.e., inferior alveolar injections) and can enhance epidural and other types of injections as well. The elongated handle 27 is advantageously about 15 cm long (about 6 inches), or in the preferred range of about 10 to 20 cm long, with tubing 22 of about 122 cm long (about 48 inches).

Automated Fluid Delivery System

As described above, the system 5 includes a fluid delivery system 50 for providing a controlled flow of medication to the injection assembly 10. Preferably the fluid delivery system is an automated system and in the present instance is a computer controlled fluid delivery system referred to as a drive unit 50.

Referring to FIGS. 1-4, the drive unit is designed to work in connection with a disposable injection assembly 10. The drive unit has a semi-cylindrical syringe cradle 52 disposed in an upper surface of the drive unit 50 as shown in FIG. 2. The cradle is configured to receive the syringe 18 of the injection assembly 10. A pair of spring-loaded clamps engage the syringe to retain the syringe in the cradle 52. A transverse slot in the cradle is configured to engage the finger flange 88 on the end of the syringe barrel. In this way, the finger flange of the barrel cooperates with the slot 55 to impede axial displacement of the syringe barrel relative to the cradle 52. The cradle 52 further includes a portion configured to receive the plunger 70 of the syringe 18. As shown in FIG. 1, the cradle is elongated so that the cradle can receive the barrel of the syringe and the plunger when the plunger is withdrawn to the rearward end of the plunger barrel. More specifically, the cradle is longer than the maximum extended length of the syringe so that the syringe can be positioned in the cradle without engaging the plunger when the plunger is withdraw to its maximum length from the barrel.

The drive unit 50 includes a movable stage 58 having three spring-loaded thumb flange catches or hooks 60 that are pivotally mounted to the stage 58. The drive unit 50 controls the displacement of the moveable stage to control the ejection of fluid from the syringe. Specifically, the stage 58 is moveable along the axis of the cradle 52 to advance the plunger 70 into the barrel of the syringe. Initially, the stage 58 is driven forwardly to engage the plunger. In particular, the stage is displaced forwardly (to the right from the perspective of FIG. 1) until the beveled surfaces of three hooks engage the thumb flange 72 of the plunger 70. Continued displacement of the stage 58 causes the thumb flange to wedge the hooks 60 radially outwardly until the hooks extend radially outwardly past the outer diameter of the thumb flange. Continued advancement of the stage 58 causes the angled surfaces of the hooks 60 to pass the thumb flange 72 at which point the hooks snap close below the thumb flange 72 so that the stage positively engages the thumb flange so that displacement of the stage displaces the plunger.

After the stage 58 entrains the thumb flange, a sensor in drive unit 50 senses resistance to the further movement of stage 58, and the stage stops. At this point, the plunger 70 is effectively axially fixed to the stage 58 by the engagement of the catches 60 on thumb flange 72. Therefore, any further rightward to leftward movement of the stage 58 will also move the plunger 70 to the right to expel fluid form the syringe body. Similarly, any retraction of the stage (i.e. movement to the left from the perspective of FIG. 1) will aspirate fluid back into the syringe body.

Figure 5:
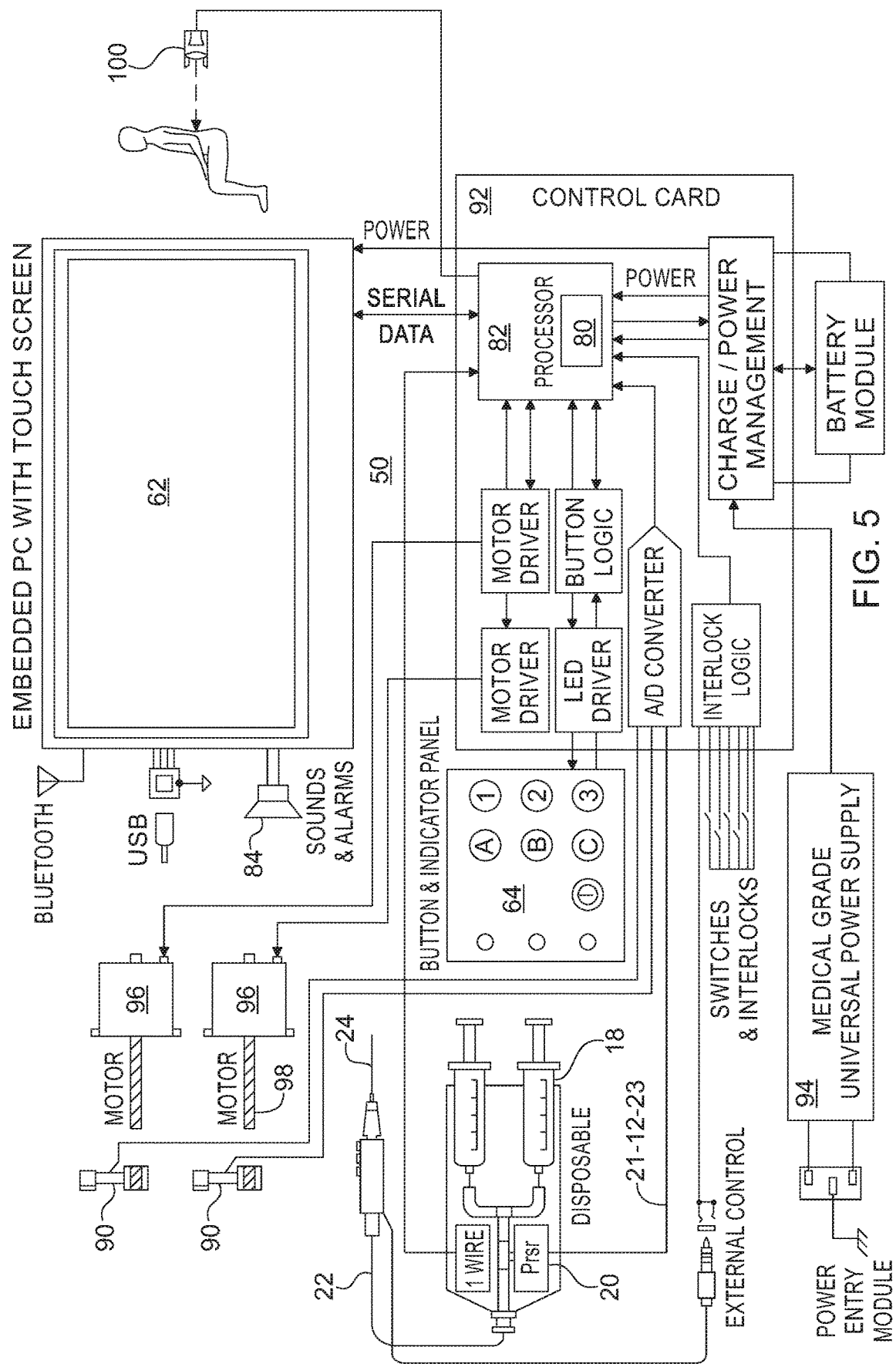
FIG. 5 is a diagrammatic view of the drug delivery system illustrated in FIG. 1.
Figure 6:
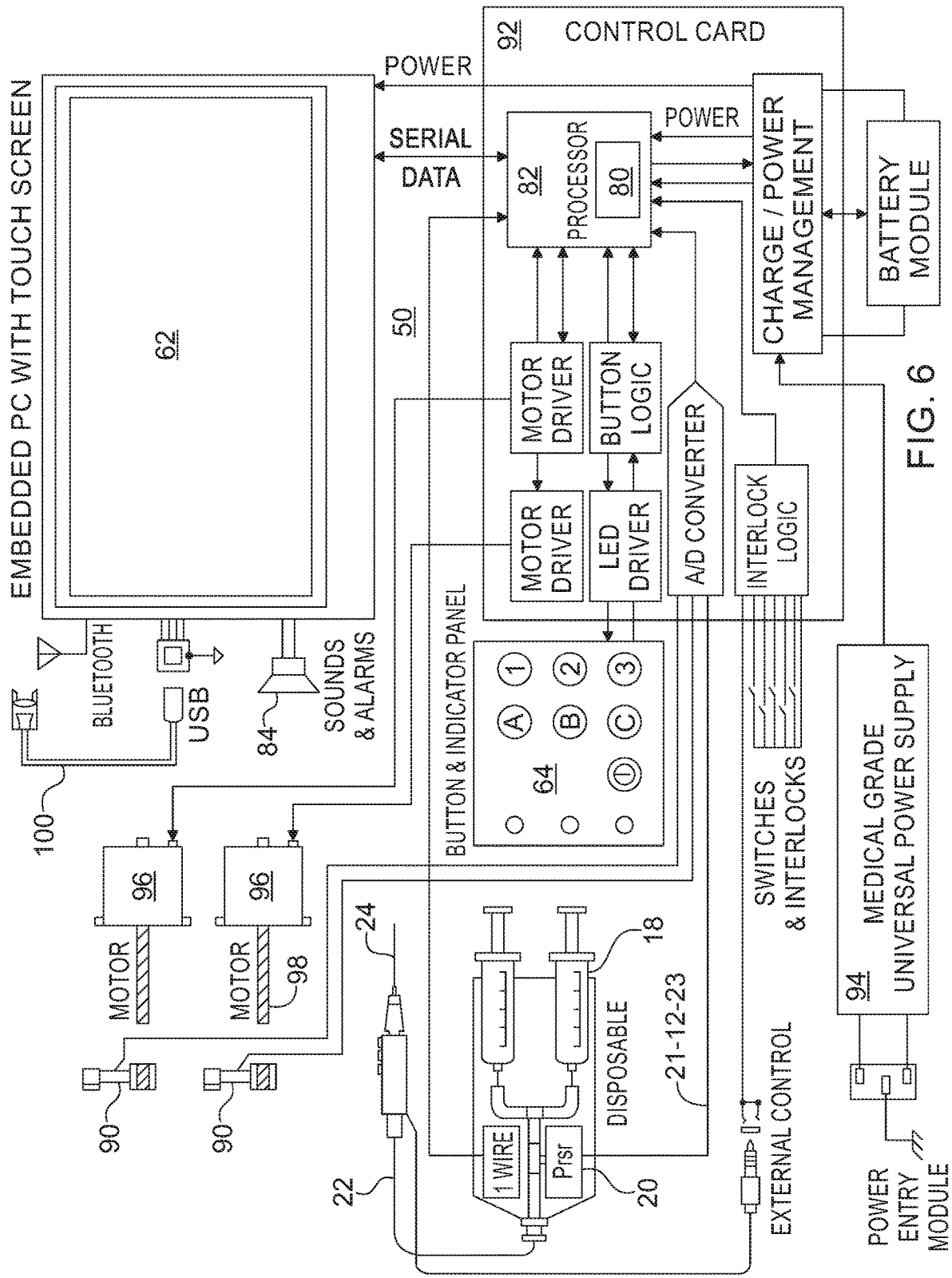
FIG. 6 is a diagrammatic view of an alternative embodiment of a drug delivery system.

The pressure sensor 20 of the assembly 10 is plugged to the proprietary connector 12 and connector 12 is plugged to the unit 50 via jack 30. The drive unit 50 houses a microprocessor or CPU 82, electronic circuitry board 92, a power supply 94 and electronic motor or motors 96 (since two syringes can be accommodated as shown in FIGS. 5-6). Each electronic motor 96 rotates a spiral shaft 98 that moves a syringe armature 90 in a forward or reverse direction. The syringe armature 90 contains a load cell sensor to detect force. Armature 90 is connected to the stage 58 to move the stage in either direction. As also mentioned, the disposable injection assembly 10 comprises an Identification-Connection component 12, syringe 18, in-line pressure transducer 20, tubing set 22 and needle 24.

The drive unit 50 is operable to provide constant or variable fluid flow. In the present instance, the drive unit may provide a non-continuous fluid-flow in response to signals received from the electronic pressure-transducer 20, which continuously senses the pressure of the fluid during an insertion/injection procedure. Based on a pre-determined pressure, the drive unit 50 may stop the flow of fluid when the detected pressure exceeds a pre-defined threshold. The pre-defined threshold may be set by the practitioner and stored in a memory 80 of a microprocessor or computer 82 of the electronics in drive unit 50. Similarly, based on a pre-determined pressure, fluid-flow will resume when the fluid pressure falls below a pre-determined pressure. The same pre-determined pressure may be used to control the stopping and re-starting of the fluid flow. In such case the pressure will build as fluid initially enters the tissue to a pre-determined level and then stop until the pressure drops below this pre-determined level. Once the fluid pressure falls below the pre-determined level, the fluid-flow will resume. In this way, the flow of fluid may start and stop during the procedure creating a non-continuous fluid flow.

The system may include pre-defined pressure thresholds used to control the flow of medication from the syringe 18 during the procedure. This enables a clinician to selectively inject drugs into specific sites and intended tissues for diagnostic and therapeutic procedures. Preselected maximum allowable pressure limits and/or flow rates are stored in memory 80 and define either the maximum recommended pressures that patients usually tolerate, or other criteria. As the pressure approaches this limit, a visual and/or audible alarm is generated for the clinician, i.e. on screen 62 and via speaker 84 that is activated by data from the microprocessor 82. In addition, data descriptive of the whole injection process is stored for future analysis in memory 80.

The system 5 may directly measure the fluid pressure in the injection assembly 10 or the system may measure a characteristic indicative of the fluid pressure in the injection assembly. For instance, the pressure may be measured by detecting the pressure resistance measured during infusion. The pressure resistance measured is converted into a visual signal on a continuous basis during the insertion procedure. However, the flow rate of medication during the procedure may be based on the fluid pressure detected in real time during the procedure. Therefore, the flow rate of the medication is variable and is dependent on the pressure in the system. In this way, the fluid pressure may be the primary controlling variable of the system.

The flow-rate, therefore, becomes a secondary variable that is modulated within a pre-determined range in order to maintain the desired fluid-flow. In one specific embodiment, the fluid flow is stopped when the pressure exceeds a pre-determined threshold (maximum pressure). The flow-rate, as a secondary variable, may be limited so that fluid injections are not unduly rapid under low pressure conditions. It is contemplated that the relationship between pressure and fluid flow rate may either be binary or continuous. A binary relationship exists when the injection device is configured to deliver a fluid at a single, pre-determined flow rate for any pressure less than the pre-set maximum. Thus, the fluid flow is either on or off based on whether or not the pressure exceeds the threshold. Alternatively, the flow rate may be modulated as a function of pressure. In this case, flow rate will be reduced as the maximum pressure is approached and increased as the pressure drops. Optionally, the flow rate may be limited to a first pre-set maximum pressure and a flow rate resumes at a second distinct pre-determined pressure.

As mentioned above, the system 5 may include a mechanism for displaying relevant injection data including, for example, instantaneous flow rates, pressures, and injection amounts upon a screen 62 of the drive unit 50. Similarly, the system may include a mechanism for recording such information for subsequent analysis after the procedure is performed. For instance, the system may include a non-volatile electronic storage medium, such as a hard drive, flash drive, optical drive or other medium for storing electronic data.

All measurements and information may be presented to the clinician in "real-time" so that the clinician may determine whether the injection is being delivered to the intended location and/or correct tissues and may modify the injection technique accordingly. In addition, the measurements may be recorded for later review and documentation of the clinical event.

It is also contemplated that multiple syringes driven by separate syringe plungers may be used to allow multiple drugs to be injected as well as a second syringe drive that does not required a pre-determined pressure to be reached for any said purpose. The second drive can be programmed on a specific flow-rate to allow infusion of a drug such as local anesthetic and other therapeutic drugs into a variety of tissues.

In yet another embodiment the device may contain two distinct syringe drives in which both are capable of modulation based on fluid-pressure as previously herein described.

Visual Indicator of Fluid Pressure

Referring again to FIG. 1, the system includes a visual signal generator 100 for providing visual signals corresponding to the fluid pressures detected by the system. The visual signal generator 100 provides feedback to the operator to guide the operator in the insertion of the needle 24 into the subject. In particular, the visual signals from the visual signal generator 100 provide continuous signals relating to the proximity of the needle tip to the intended location, such as a fluid-filled space.

The visual signal generator 100 may be any of a variety of lights. For instance, referring to FIG. 1, the visual signal generator may comprise a light head 105 mounted on the end of a flexible cable 102. The flexible cable 102 may have sufficient rigidity that the cable can be bent into a desired position and orientation and retain that position without external support. In this way, the operator can position the light element so that the light head 105 is directed toward a surface that is within the field of view of the operator while the operator is focused on the insertion site on the patient. For instance, the light from the light element may be projected onto a surface adjacent the subject, such as a wall or other planar surface. Alternatively, and preferably, the light head 100 can be positioned so that the light head projects a beam of light toward the patient. For instance, the light from the light element can be aimed directly onto the skin or clothing of the subject. More particularly, the light may be projected onto the patient adjacent the insertion site so that the light signals from the visual signal generator 100 are within the operators field of vision while the operator is visually monitoring the insertion site. In this way, the visual signals from the visual signal generator 100 provide the operator with useful information regarding the injection without forcing the operator to look away from the injection site.

The light head 105 may include any of a variety of light elements. For instance, the light head 105 may include a light emitting diode, an incandescent light, a laser diode or any other light emitting element. Additionally, the light element 105 may comprise a plurality of such light emitting elements. Further still, the light element 105 may include a plurality of light elements of varying light intensity, color and/or coherence. Although the light head 105 may include one or more diffuse light elements, preferably the light head 105 provides a beam of light that is sufficiently coherent to project onto the patient and be readily discernible by the operator during a procedure. For this reason, the light head 105 may include a lens 107 to focus the light from the light element(s) as shown in FIG. 2.

The light produced by the visual signal generator 100 is controlled by the drive unit 50. In particular, the visual signal generator 100 is controlled in response to electrical signals from the microprocessor 80 of the drive unit 50. The drive unit may include a separate control circuit that drives the visual signal generator 100 in response to control signals received from the microprocessor 80 of the drive unit. More specifically, the controller for the light circuit may be configured to separately control each of a plurality of light elements in the light head 105. The light control circuit may control each light by controlling whether the light element is illuminated or not. The light control circuit may control the intensity of each light element. Further still, the light control circuit may control combinations of the light elements to change the light provided by the visual signal generator. For instance, the light control circuit may illuminate combinations of light elements to change the color of the light provided by the light head 105. For instance, the light head may include a plurality of red, green and blue light elements and the light controller may selectively control the illumination of the differently colored light elements to create a light beam of red, yellow or green or any of a variety of colors.

Further still, the light control circuit can control the light elements to create varying patterns for the light projected by the visual signal generator. For instance, the visual signal generator may project a light beam having a particular pattern. In one example, the visual signal generator 100 projects a first colored signal when the pressure sensor 20 detects pressure within a first range; and the visual signal generator may project a second colored signal when the pressure sensor detects a pressure within a second range. Additionally, when the pressure sensor detects a signal nearing the threshold between the first range and the second pressure range, the visual signal generator may project a beam wherein a distinct part of the beam is the first color and a distinct part of the beam is the second color.

In addition to controlling the light intensity, color and pattern, the light control circuit may control the frequency of the light. Specifically, the light may be intermittent so that the light beam flashes on and off. The frequency of the on/off cycle can be controlled in response to the pressure detected by the system. The light control circuit may control the visual signal generator based on the absolute value of the detected pressure. Alternatively, the light control circuit may control the indicator based on the relative value of the detected pressure, meaning the current value relative to the most recently detected pressure. In this way, the light control circuit can vary the light based on whether the pressure is increasing or decreasing. Similarly, the light control circuit can control the light based on both the absolute and the relative value of the detected pressure. For instance, the light control circuit can control the light elements to produce a beam of light having a certain color based on the detected pressure being within a particular pressure range. Additionally, based on the relative pressure indicating that the pressure is rising, the light control circuit may cause the visual signal generator to blink the select color. Further still, the light may be controlled so that the frequency of the blinking increases as the pressure increases to the upper end of the pressure range. Once the pressure increases beyond the pressure range so that the pressure is at the low end of a second pressure range, the light control circuit may control the visual signal generator so that it provides a different color light blinking at a lower frequency while the pressure is at the low end of the second pressure range.

As can be seen from the foregoing, the visual signal generator 100 can provide a myriad of colors and patterns that can provide continuous feedback signals for the operator to use as guidance during the needle insertion procedure. A few examples of the manner in which the visual signal generator 100 may provide continuous light feedback signals will now be described.

As discussed above, the visual signal generator may project a beam of light onto any of a variety of surfaces that allow the operator to see the light signal while maintaining focus on the injection site. In the following discussion, the light will be described as being projected onto the patient. It should be understood that this is merely intended as an exemplary surface onto which the light is projected.

The drive unit 50 may be programmed so that the visual signal generator projects a yellow light when the detected pressure is within the range of 0-20 mm/Hg, a green light when the detected pressure is within the range of 20-40 mm/Hg and a red light when the detected pressure is within the range of 40-200 mm/Hg. The light may blink while the pressure is increasing. Therefore, the visual signal generator will project a blinking yellow beam onto the patient as the needle is inserted into the patient and the pressure increases between up to the threshold of 20 mm/Hg. Once the pressure increases to 20 mm/Hg, the indicator light changes so that a beam of green light is projected onto the patient. And the light will blink as long as the pressure increases. If the pressure remains steady, the light will remain lit (i.e. will remain illuminated but will not blink). Further still, as the needle is advanced and the pressure increases toward 40 mm/Hg, the frequency of the blinking will increase until the pressure reaches 40 mm/Hg. At that point, the frequency of the blinking will reduce significantly and the color of the light will change to red.

In the foregoing description, the visual signal generator provides a continuous feedback signal corresponding to the detected pressure so that the operator can readily discern various data about the detected pressure, including but not limited to pressure, rate of pressure change and whether the pressure is increasing, decreasing or not significantly changing. It should also be understood that the visual signal generator may provide color signals that indicate a warning, an alarm, a system error or failure or any other of a variety of system issues that would demand attention by the operator. For instance, in the foregoing example, the color red is used to indicate that the fluid pressure is within a particular range. Alternatively, the color red (or any other color) could be reserved to indicate a warning, error or other alarm. In this way, when the visual signal generator 100 projects a red beam or a blinking red beam, the operator is readily alerted to an issue that requires attention.

Further still, in the foregoing discussion, the visual signal generator 100 provides a beam that corresponds to a certain condition or characteristic of the exit pressure for the injection assembly. It should also be understood that the lack of light from the visual signal generator may also be used to provide information to the operator. For example, the visual signal generator may be off so that no light is projected when the pressure falls within a certain range. For instance, if the pressure is below 10 mm/Hg the visual signal generator may be off.

In addition to a variety of colors and patterns, the visual signal generator 100 may provide graphical and/or human readable graphics, including, but not limited to numbers, letters and symbols. For instance, the visual signal generator 100 may project the numerical value of the pressure detected by the pressure sensor 20. In this way, the operator will easily see the change in pressure in real time without having to take his or her focus off of the injection site and the needle that is being manipulated. Additionally, the graphical information can be combined with changes in color or pattern to provide further information to the operator. By way of example, the visual signal generator may project the numerical value of the pressure detected in real time. Additionally, the color of the numerals projected may change as the pressure value moves from one pressure range to the next as discussed further above. Similarly, the number may be projected in a constant color, such as a dark color, and the numbers may be embedded within a background having a color that relates to a particular pressure range or other characteristic as described above.

It should be understood that the graphical information projected by the visual signal generator need not be limited to alphanumerical characters. The visual signal generator may provide any of a variety of types of graphical data. For instance, the visual signal generator may project a plot of the detected pressure values over time so that the operator can see a graphical representation illustrating the change in pressure, including the magnitude of the change, the rate of the change and various inflection points on the graph. Similarly, the data displayed need not be limited to the real-time pressure values detected by the pressure sensor 20 or otherwise. The data projected by the visual signal generator may include information such as the flow-rate of medication or fluid through the injection assembly 10, the fluid volume in the syringe, elapsed time since the start of the needle insertion, and patient data. Accordingly, it should be understood that the visual signal generator can be configured and controlled to project any visual data that could be provided on a display screen, such as an LED, LCD or CRT screen. The visual signal generator will project such visual data in a manner so that it is readily viewable by the operator without having to take his or her focus from the needle being manipulated.

In the foregoing description, the visual signal generator 100 is a light element that projects visual feedback for the operator to use to guide the insertion of the needle into the subject. In the foregoing embodiments, the visual signal generator 100 is on a semi-rigid arm or cable connected to the drive unit so that the light element can positioned at a desired location and angled to project light at the desired target location. Referring to FIG. 4, an alternate visual signal generator 200 is illustrated. In the alternate embodiment, the visual signal generator is mounted on and/or connected directly to an element of the disposable injection assembly 10. In particular, the injection assembly 10 includes an elongated hub 27 connected to the fluid tubing 22. The hub 27 includes a mounting element for connecting a needle 24 to the hub. For instance, the hub 27 may include a Luer connector.

As shown in FIG. 4, the visual signal generator 200 may be mounted on or otherwise connected to the elongated hub. In this way, the hub 27 provides an elongated rigid element for supporting the visual signal generator 200. The visual signal generator projects the visual signal forwardly, such as onto the patient at or adjacent to the injection site. In this way, the visual signal generator may project a beam having an axis that is parallel or substantially parallel to the axis of the needle 24. The visual signal generator includes an elongated cable 206 so that the visual signal generator can be extended away from the drive unit 50. In particular, the cable 206 includes a connector for connecting the visual signal generator with the drive unit to receive control signals from the drive unit as described previously in connection with the above embodiment.

Mounted on the hub 27, the visual signal generator 200 is positioned to project a light beam toward the injection site. In particular, the visual signal generator is mounted so that at least a portion of the light beam 202 emitted from the visual signal generator is parallel with the axis of the insertion needle 24. More specifically, the visual signal generator may be connected with the needle so that a substantial portion of the light beam 202 is parallel with the axis of the needle.

Yet a further alternative embodiment of a visual indicator is a light element, such as one or more fiber optic elements that provide a visual light signal around or through the elongated tube 22 of the injection assembly 10. In this way, the light can project into the fluid in the tube so that the light signal is adjacent the needle due to the fact that the needle is connected to the tubing and the light is projected onto the needle or the patient by virtue of the fiber optic elements extending along the length of the hose 22. Accordingly, it should be understood that the visual signal generator may be configured in a variety of designs that provide a visual signal projected on a surface readily viewable by the operator without changing focus from the injection site.

Thus, advantages of the present device over the prior art include:
  (i) a mechanism for projecting an image representative of the exit-pressure value upon the surface of a patient so that one can determine when the fluid filled tissue space such as the epidural, intra-articular, globe of the eye, cysts and blood or other fluid vessels, but not limited to these structures, has been identified;
  (ii) a mechanism configured to enable the operator to continuous maintain the field of view to the needle entry site of the patient while projecting information at the needle entry site, eliminating the need for a remote visual screen or the need to view a screen to obtain such visual information;
  (iii) a mechanism operable to monitor exit-pressure as a series of predefined ranges in which the light emitting source enables the operator to objectively distinguish between thresholds between different ranges via a distinct visible change, such as a change in color; and
  (iv) a mechanism operable to monitor exit-pressure by a projected visual image capable of using flashing patterns, and or blinking patterns to communicate an ascending or descending progression of exit-pressure. Included in this is the ability to communicate via a lack of change in pressure by providing a visual indication.

Calculation of Fluid Pressure at the Exit of the Needle

As discussed above, the fluid pressure is used to control operation of the system 5. For instance, the visual feedback provided by the visual signal generator 100 is based on the determined fluid pressure. There are several methodologies for calculating the fluid pressure at the exit of the needle.

A pressure sensor may detect the fluid pressure in the injection assembly 100. For example, as discussed above the pressure sensor may be an in-line pressure sensor, such as that available by Merit Medical part #0001. Alternatively, a pressure sensor internal to the drive unit 50 may detect the fluid pressure between the syringe 18 and the tubing set 22. Another alternative is using a thumb-pad force sensor to detect the force driving the plunger to calculate the pressure within the syringe. A command signal from the pressure sensor sends data of pressure to the CPU for calculation to determine the exit-pressure. Exit-pressure is calculated by a mathematical formula that subtracts the head-pressure of each of the components proximal to the point of pressure measurements. In addition, a calculated value is provided related to a counter head-pressure that is correlated to specific pace (i.e., rate) of forward movement of a needle through bodily tissues. Thus, a pressure value is input and a calculated pressure value is calculated by taking into account all the anticipated resistances of the system to calculate a final unbiased exit-pressure value. The CPU of the drive-unit calculates the values on the input and preset values available within the software. The final calculated exit-pressure value is used to control the CPU and is used to control the motor that controls the flow of fluid from the syringe 18.

As mentioned above, a counter head-pressure may be subtracted from the pressure measurement to determine the final value of the fluid pressure. The counter head-pressure varies in response to the rate of insertion and the counter-head pressure is subtracted from the measured fluid pressure when calculating the fluid exit pressure. For instance, the following values represent the counter-head pressure values for a variety of insertion rates.

| Rate of Forward Movement PACE mm/sec | Counter-Head Pressure |
|---|---|
| 0.10 | 1.25 mm/Hg |
| 0.50 | 6.25 mm/Hg |
| 1.00 | 12.50 mm/Hg |
| 1.50 | 18.75 mm/Hg |
| 2.00 | 25.00 mm/Hg |
| 2.50 | 31.25 mm/Hg |
| 3.00 | 37.50 mm/Hg |
| 3.50 | 43.75 mm/Hg |
| 4.00 | 50.00 mm/Hg |
| 5.00 | 62.50 mm/Hg |
| 6.00 | 75.00 mm/Hg |
| 7.00 | 87.50 mm/Hg |
| 8.00 | 100.00 mm/Hg |
| 9.00 | 112.50 mm/Hg |
| 10.00 | 125.00 mm/Hg |
| 20.00 | 250 0 mm/Hg |

Since the rate of insertion significantly affects the counter-head pressure, it is desirable to control the rate of insertion of the needle. Accordingly, the system may incorporate a handset 300 designed to aid the user in inserting the needle in a controlled and known insertion rate. In the present instance, a re-useable handpiece is utilized. However, it should be understood that features of the handpiece can be utilized in a disposable needle assembly.

Figure 10:
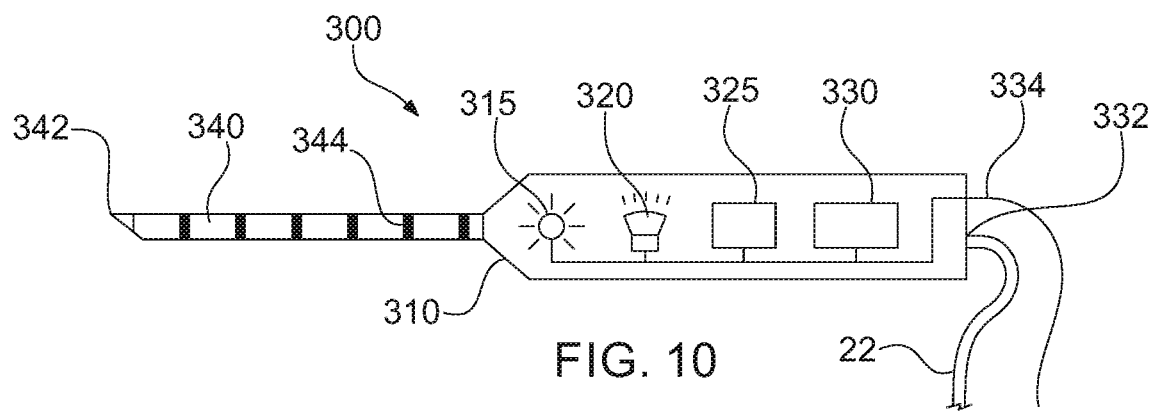
FIG. 10 is a side view of an alternate needle assembly operable in connection with the drug delivery system illustrated in FIG. 1.

Referring to FIG. 10, the handpiece 300 includes a hollow housing 310 and an elongated hollow needle 340 projecting forwardly from the housing. A connector 332 is provided for connecting the handpiece with the fluid line 22 of the injection assembly 10. Specifically, the connector 332 provides a fluid-tight seal for connecting the handpiece 300 at the rearward end of the housing to facilitate connection of the handpiece with the fluid in the syringe. The fluid flows to the handpiece and out through the needle 340.

The needle 340 includes a plurality of markings 344 along the length of the needle. In particular, the markings include a plurality of lines transverse the axis of the needle. The markings 344 are spaced apart from one another a known distance. More specifically, each marking 344 is spaced apart from the adjacent marking by a uniform distance. The markings preferably extend along at least a substantial portion of the length of the needle. In the present instance, the markings extend from the tip 342 of the needle 340 to the connection point between the housing 310 and the needle. The increments on the surface of the needle may be a laser etching, alternating colors or engravings on the surfaces of the needle at defined distance, such as 1.0 cm increments as an example.

The handpiece 300 may further include an indicator light 215 configured to provide the operator with regular prompts. The indicator light 315 may be an LED or other light element that flashes at a predetermined frequency based on the intended rate of insertion. Specifically, prior to commencing a procedure, the operator enters various data regarding the procedure and based on the data entered by the operator an insertion rate is determined for the procedure. Based on the insertion rate, the frequency of the blinking indicator 315 is determined. As discussed further below, the indicator light operates similar to a metronome providing a constant pacing element for monitoring the rate of insertion of the needle to improve the accuracy and consistency of the insertion rate of the needle.

The handpiece further includes an audible indicator 320 such as a piezoelectric audio indicator for providing an audible signal, such as a buzz, tone or chime. The audible indicator 320 operates similar to the indicator light 315 by providing a regular tone that can be used to pace the insertion rate of the needle 24.

Additionally, a control button 325 may be provided for the handpiece. The control button 325 may operate as an on/off button. However, the control button may also be operable to enter various control commands. For instance, the control button 325 may be operable to over-ride one or more operations of the drive unit 50 as discussed further below.

Finally, the hand set 300 may also include an output mechanism, such as a display screen for displaying various information, such as the frequency of the indicator light 315 and/or audible indicator 320. Additionally, the display may show additional information, such as real-time pressure values, or alerts "Proceed", "Reposition", "Inject", Flow-rate 1, Flow-rate 2, Low-Speed, High-Speed, "Aspirating".

As described above, the hand set includes both a visual and audible indicator 315, 320. It should be understood that the handpiece does not need to include both an audible and a visual indicator; it could include just a single indicator. Further still, although a visual and audible indicator are described, a variety of alternate indicators could be used instead, such as a vibration element that provides regular vibration indicator signals.

The defined audible/visual cadence directs the operator to advance the needle forward a defined increment based on the markings 344 on the needle. The forward movement of the specific increment is referenced upon the penetration of the surface of the needle into the surface of the skin, dermis or body part the needle is penetrating. A rate of 0.5 cm/sec to 2.0 cm/sec is provided as a range of movement of the needle.

The precise rate of movement is achieved by coordinating the audible or visual cadence to the movement of the needle markings that penetrates the surface and is noted by the visual markings on the surface of the needle at specific distances. The marked needle is then advanced one increment thru the surface of the tissue per "beep" and/or "blink".

The rate of audible and/or visual cues is pre-set in the CPU and activated upon fluid flow. A range of 0.5 cm/sec to 2.0 cm/sec is provided however it is understood that any rate of movement coordinated incremental movement of a needle displaying markings is anticipated. This forward rate of movement selected from the pre-set values will enter a corresponding counter-head pressure value that will be subtracted from the calculation in determining an objective tissue pressure value.

An example of an operational rate is the operator advancing the needle 1.0 cm for each beep sound and visual "blinking" of the LED to provide coordination of a precise needle advancement rate. This design enables a precise rate of needle advancement to be maintained. Additionally, while the needle is being advanced a continuous flow of fluid from the needle is provided and real-time, continuous pressure monitoring is provided.

As noted above, the handpiece 300 may include a control button. The control button may be utilized when the needle is not being advanced. In such an instance, pressing the button operates to provide a control signal to the drive unit 50 so that a counter-head pressure value will not be subtracted from the calculation of the exit-pressure (since the needle is not being advanced there is zero or essentially zero counter-head pressure). It is understood that the button or control on the handpiece 300 may also be activated to correspond with the forward movements in which the counter head-pressure is subtracted from the calculation of the head-pressure therefore providing a means to distinguish between when the needle is being advanced and when it is remaining stationary within the tissues. In this way, actuation of the button 325 during periods of minimal to zero needle insertion promotes accuracy of the exit-pressure values within the tissues during the procedure. In addition to the switch or control button discussed above, the handpiece may include a second button or control element in which backward movements would add an additional head-pressure value to compensate for the backward movement which causes a decrease in exit-pressure values when moving a needle backward through the tissues.

In the description above, the handpiece incorporates a visual or audible indicator 215, 220 to pace the rate of insertion of the needle. Although the indicator(s) may be provided on the hand piece, the visual signal generator 100 described above can be used to provide the visual signals for pacing the rate of needle insertion. Specifically, the visual signal generator 100 may project a visual signal at a constant and defined rate or frequency similar to how the indicator light 315 blinks. Since the visual signal generator 100 projects light adjacent or in the field of view of the injection site, the operator can see the signal from the indicator light to pace the needle insertion. Therefore, as mentioned above, the needle can be used separately from the rest of the features of the handpiece. Specifically, a needle with markings for guiding the rate of insertion can be used with a typical injection assembly, such as injection assembly 10 described above. In such an embodiment, the visual signal generator will provide the visual cues for guiding the rate of insertion of the needle.

Since skin color will tend to vary from patient to patient, it may be desirable to incorporate an element that will render the indicator signals more uniform when projected onto the patient. For instance, it may be desirable to attach a background element onto which the visual signal can be projected. An exemplary background element would be a flexible patch that can be applied directly to the skin of the patient adjacent the intended insertion site. The patch may be formed of any of a variety of flexible materials, such as fabric, paper or plastic.

The patch has a front side onto which the visual signals are to be projected and a backside configured to be attached to the patient. Preferably, the backside incorporates an adhesive backing so that the patch can be readily applied directly to the skin of the patient. Any of a variety of known adhesives for removably connecting a bandage to a patient may be used for the adhesive backing. The front side of the patch may be formed of any of a variety of patterns, but preferably, the front side is a solid color. Further still, preferably the color of the patch is selected to improve the contrast between the projected visual signal and the patch. For instance, if the projected visual signals are generally dark colors, the patch may have a lightly colored hue, such as white or off-white. Conversely, if the projected signals are generally light colors, the patch may have a dark hue, such as black.

Configured as described above, the adhesive backing of the patch may be pressed against the patient to adhere the patch to the patient. Preferably the patch is applied adjacent the intended insertion site, such as on the patient's back, adjacent the spine. The visual signal generator is aimed at the patch and the visual signal generator then projects visual signals as described above.

Method for Administering Injections into a Fluid-Filled Space

An exemplary method for administering an epidural injection using the system described above will now be described. It should be understood that the present system is not limited to use in epidural injections. Accordingly, it should be understood that the principles and methods described below may be readily adapted for injections into tissues and anatomical areas other than the epidural space.

Connective tissues of the body have been shown to produce pressures above 200 mm/Hg when injected with a fluid at a rate of 0.07 mL/sec. Each tissue has its own pressure density characteristics which are represented as measurable pressures that can be elicited within a given tissue type. The density or resistance of the tissue is measured using the pressure of a fluid infused from a computer-controlled drug delivery system capable of detecting pressure resistance during infusion. It has also been demonstrated that fluid-filled spaces such as the epidural tissues, the intra-articular space of joints, or vessels of the body have pressures when measured during injection that are well below 200 mm/Hg. In fact, fluid-filled spaces have been found to have significantly lower pressure resistance to fluid-flow and typically have pressure resistances closer to zero mm/Hg when infusing into this fluid-filled tissue sites.

The first pre-determined upper pressure limit is determined by the clinician. Typically, the first pre-determined upper pressure limit is not greater than 200 mm/Hg. When using such a setting, the injection system 50 will administer a negligible amount of medication into the connective tissues and then by selecting a second predetermined pressure below 50 mm/Hg at which the fluid flow will resume. Hence the needle is properly positioned within the fluid-filled space of epidural tissue-space because the pressure within the epidural tissue space is believed to be between about +15 mm/Hg and −15 mm/Hg, whereas the pressure associated with the Ligamentum Flavum is above 200 mm/Hg.

The pressure measurements within the extra-ligamentary tissues are typically about 100-200 mm/Hg. With the injection device 50 having a second pre-determined pressure at which the fluid flow will resume, that is 50 mm/Hg or below, there will be no significant fluid flow once the needle enters the subcutaneous tissues as the pressure will quickly rise and be maintained as long as the needle resides within the subcutaneous tissues (extra-ligamentary tissues). The clinician will advance the Tuohy needle and encounter the ligamentum flavum. Still no fluid flow will occur because, as noted above, the ligamentum flavum generates a pressure greater than 100 mm/Hg. Upon penetrating through the entire thickness of the ligamentum flavum (i.e., needle entry into the epidural fluid-filled space) the pressure will immediate drop below 50 mm/Hg triggering an optional visual display and/or audible tone and/or spoken word such as "Located Epidural". At this point, the drug-containing fluid will begin to flow into the intended target site. Thus a non-continuous fluid-flow is utilized to identify the targeted tissues. It is possible that the first and second pre-determined pressure values are set to the same number to allow fluid flow to occur only after the pressure drops below a pre-determined pressure.

The pressure sensor 20 or plural sensors of the injection device 50 provide an automatic safety feature in the event that the injection needle leaves the epidural tissue space (e.g., from clinician error or patient movement) or its patency is compromised. If the needle 24 leaves the epidural tissue-space, either by withdrawing through the ligamentum flavum or by contacting the dura, the pressure will immediately rise to a first selected pressure P1, causing a slowing and eventual stoppage of fluid flow at fluid pressures >200 mm/Hg. This has been shown to occur within approximately 2 seconds time (see, Ghelber-Regional Anesthesia and Pain Medicine Vol 33 No 4 2008, page 349 FIG. 2). Optionally, this change in pressure from <50 mm/Hg to >200 mm/Hg will again trigger a visual and/or audible alarm to alert the clinician of improper needle placement. Flow will again automatically resume once the needle is reestablished in the epidural tissue space and the instantaneous pressure at the needle point drops below P1, or, in a further embodiment of the invention, when the pressure drops to a second selection pressure P2 of equal to or below 50 mm/Hg. This automatic safety feature of the injection device helps prevent injection of the anesthetic solution into the spinal cord.

Figure 8:
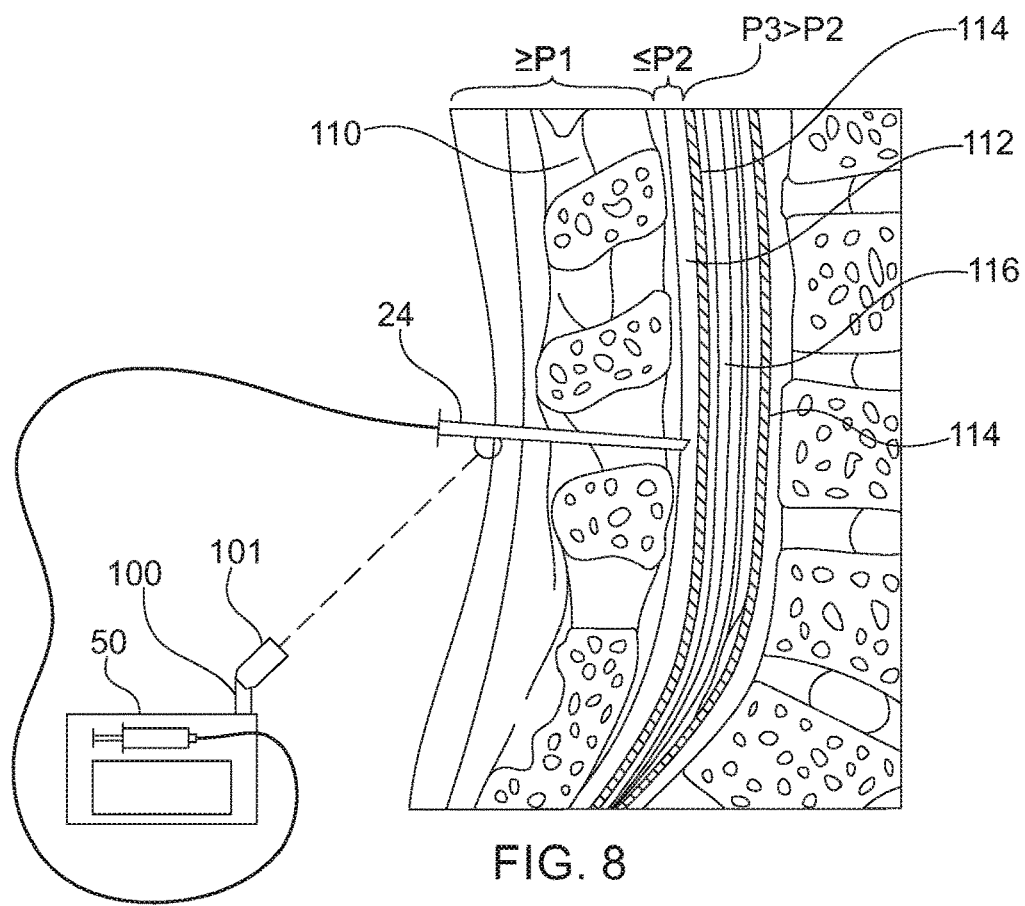
FIG. 8 is an enlarged fragmentary sectional view of a portion of a patient's spine in combination with an alternate embodiment of a drug delivery system.

Turning to FIG. 8, the area of the spine of a subject for an epidural injection is shown. Starting from the outside injection site for the point of the needle 24 at the left in FIG. 8, the tissues in this area include various layers of skin, fat and connective tissue 110, followed by the epidural space 112 that is the anatomic space of interest in one embodiment of the invention. Beyond the epidural space 112 is the dura mater 114 of the spinal cord 116. The rightward point of the needle 24 progresses through the tissues, but stops before reaching the spinal cord. Cross sections of the bones of the backbone in this area are also shown.

In the present instance, the microprocessor 82 and memory 80 are programmed with the first pressure P1, of, for example, about 200 mm/Hg, that is selected to be equal to or greater than the instantaneous fluid pressure at the point of the needle as it enters and moves through the tissue 110. At or above this pressure P1, the motor 96 is stopped and the fluid flow to the needle point stops. When the needle point enters the epidural space 112, the instantaneous fluid pressure drops to below P1 and the microprocessor causes the motor to start again to resume fluid flow, now into the epidural space 112 according to one embodiment. According to a second embodiment, the second selected pressure P2 stored in memory 80 must be reached before fluid flow resumes. In a third embodiment, when a third selected pressure P3 stored in memory 80, that is greater than P2 but less than P1, is reached, the fluid flow will stop again. Reaching this third pressure P3 indicates that the needle point has pressed into the dura 114 or is otherwise leaving the anatomic target space. The spaces or layers through which the needle point will travel are correlated to the pressure settings P1, P2 and P3 in FIG. 8.

The first selected pressure P1 for stopping fluid flow is preferable about 200 mm/Hg for an epidural injection, but can be in the range of about 25 to about 300 mm/Hg depending on the tissue to be first punctured by the needle point. Pressure P2 for resuming fluid flow is preferably about 50 mm/Hg for an epidural injection, but can be in the range of about 20 to about 150 mm/Hg depending on the anatomic space of interest. The third selected pressure P3 for stopping fluid flow again, is preferable about 125 mm/Hg for an epidural injection but can be in the range of about 80 to about 180 mm/Hg depending the anatomic space of interest. The use of three set pressure improves the flow/no-flow control as the needle point moves through different tissue types for any fluid-filled anatomic space capable of receiving fluid at a lower pressure than tissues surrounding the anatomic space.

It is contemplated that a pharmaceutical-free fluid is used to identify the epidural tissue space during the needle placement phase of the epidural procedure. Suitable pharmaceutical-free fluids include, for example, sterile saline, artificial cerebral spinal fluid, Ringers, 5% dextrose, or filtered air. Once the epidural tissue space is identified using the pressure differential, the injection fluid is changed to a pharmaceutical-containing fluid. The use of a pharmaceutical-free fluid during the needle placement phase minimizes or eliminates the delivery of the pharmaceutical to non-target tissues.

Another feature of the current device and methodology is the objective nature of pressure measured by a computer-controlled drug delivery device that is monitored during all phases of the injection process. The clinician, therefore, no longer relies on the subjective nature of a "feel" but rather is provided with objective information of absolute values while performing each phase of this critical technique. Each phase of the technique is improved by the ability to continuously monitor the pressure while using a non-continuous fluid-flow of drug allowing adjustments to be made that ensure greater safety and efficacy of the injection.

In another example, the clinician may reset the pre-determined maximum allowable pressure once the fluid-filled space is penetrated and the injection has begun. As noted above, prior to needle entry into the epidural space, the fluid pressure is greater than 200 mm/Hg so little or no fluid is being delivered. Upon entry of the fluid-filled space the pressure drops below zero and gradually rises to about 1-10 mm/Hg. This drop in pressure initiates the flow of fluid from the injection device. At this time, the maximum pre-set pressure value may be changed to a new, lower, maximum. For example, the pre-determined maximum pressure in which fluid flow stops may be reduced to 25 mm/Hg which will provide an extra level of patient safety in the event that the injection needle contacts the dura mater or is withdrawn from the epidural space. The new pre-determined lower maximum pressure will cause the fluid flow to be arrested sooner, and at lower ectopic injection amounts, than the original pre-set value. The change in pre-determined maximum pressure stop of fluid flow may be performed manually by the clinician or automatically by a control element in the injection device.

It should be understood that the example of 200 mm/Hg as the pre-determined maximum pre-set pressure for stoppage of fluid flow is an example and that either a lower or higher pre-set pressure may be selected at the discretion of the clinician. Also, the second pre-determined 50 mm/Hg pressure value at which fluid flow resumes is an example and that either a lower or higher pre-set pressure may be selected at the discretion of the clinician and is merely illustrative. The principles and techniques may be modified for an injection into almost any anatomical location. What is of particular importance in this embodiment of the method and device is the ability to define and select pre-determined values of pressure to produce a non-continuous flow of drug for diagnostic and therapeutic administration.

The techniques described herein are equally applicable to human and animal tissues.

FIGS. 5-6 illustrate schematic representations of the instrument components and electronic layout. As shown in FIG. 5, the visual signal generator 100 can be connected to the central processor 80 of the drive unit 50. In particular, as described above, the central processor 80 may include a separate light control circuit that is operable to control the light elements of the visual signal generator 100. In particular, the light control circuit may receive signals from the central processor or other elements of the drive unit and the light control circuit may control the light elements in response to the received.

FIG. 6 illustrates an alternate arrangement to the system illustrated in FIG. 5. In FIG. 5, the visual signal generator 100 is connected to the display screen 62 of the drive unit 50. In particular, the visual signal generator 100 may be connected to a USB hub on the display. In such an embodiment, the visual signal generator 100 includes a light control circuit configured to receive signals from the display and control the lights to provide the desired visual feedback discussed above. For instance, the visual signal generator 100 may be configured to operate as a remote projection screen that is able to project whatever image is displayed on the display screen 62.

Figure 9:
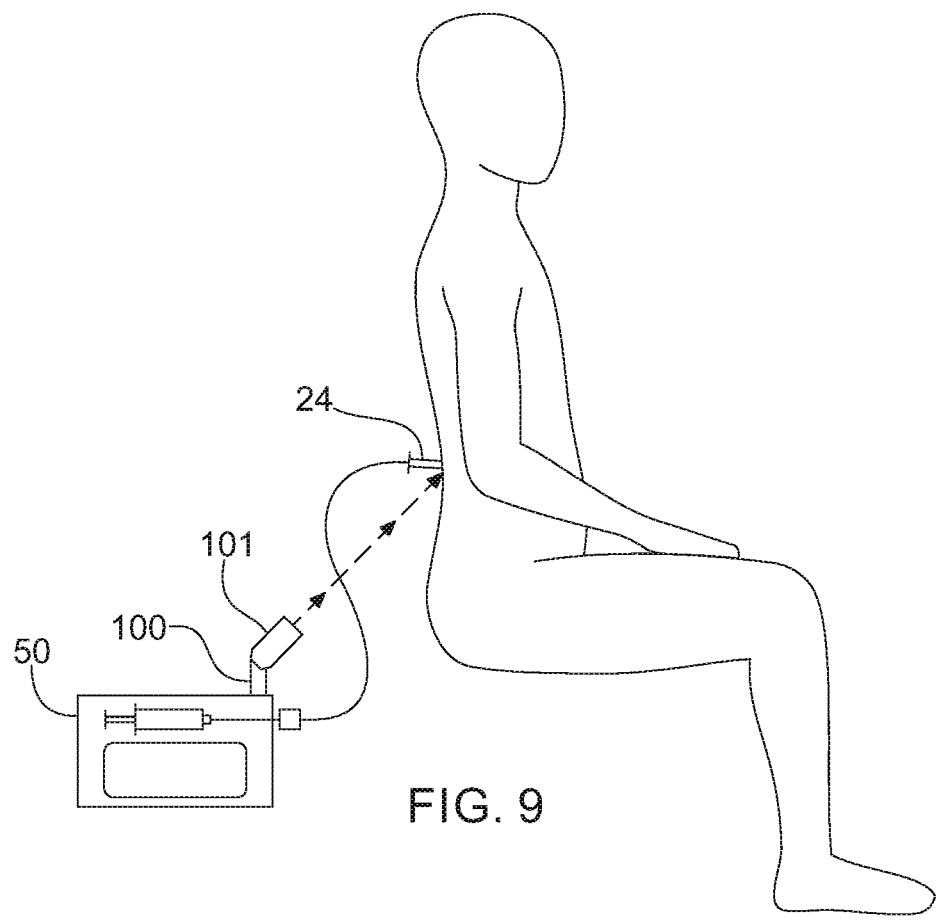
FIG. 9 is a diagrammatic view of the drug delivery system illustrated in FIG. 8 illustrated in use with a patient.

FIG. 9 illustrates the drive unit with affixed light source 100 projecting light image upon the surface of the patient at the target and site to which a needle has entered the patient. The light communicates that the needle has detected the fluid filled cavity by a color change projected upon the surface of the patient.

Using emitted light projected upon the surface of a patient has multiple benefits that are not be realized by other mechanisms. In particular, a light emitting element capable of emitting a variety of colors and/or light patterns provides:
  (i) a mechanism operable to objectively represent one or more specific pressure threshold(s) that cannot be communicated with a continuous acoustic tone;
  (ii) a mechanism designed to efficiently notify the operator when the pressure is ascending or descending without subjective interpretation, by varying colors and/or light patterns that are objectively recognizable visually as distinct indicators;
  (iii) a mechanism allowing the operator to focus his or her field of view on the treatment site, and in particular, one in which viewing a remote display screen is not required to confirm an audible tone or other signal;
  (iv) an inexpensive mechanism for communicating information without the need for a remote display screen or auxiliary equipment;
  (v) a mechanism that avoids limitations of acoustic feedback in an operating room when there are many competing sounds and monitoring devices that may confuse the operator and lead to medical errors; and
  (vi) a mechanism that avoids sounds that the patient may interpret as anxiety producing when performing a procedure.

Methodology for Epidural Insertion

The top view of the instrument shows the recessed cavity 52 and recess 56, together called the syringe cradle, which allows the drive unit 50 to receive a standard 20 cc syringe 18. Contained within the plunger recess 56 is the movable armature 90 and stage 58 that engage the thumb pad or flange 72 of the disposable syringe 18. The mechanism that engages the thumb pad of the syringe has the series of spring loaded hook 60 shown FIG. 1, which automatically capture the syringe thumb pad.

As shown in FIG. 1, as the thumb pad 72 is engaged, the spring loaded hooks 60 will move outward, over and then engage the thumb pad in hook-like fashion. This action will secure the thumb pad as shown in FIG. 1, allowing the syringe stage 58 to mechanically move the syringe plunger 70 in either direction, thus ensuring that aspiration can be performed. Additionally a force sensor is integrated into the design of the syringe armature 90. The syringe armature 90 uses optical and mechanical features to identify the position of the syringe and can calculate the volume of fluid in the syringe.

Step 1: The drive unit 50 is turned "On" via a separate side-panel 64 as shown in FIG. 5 that includes "On/Off", "Start/Stop", "Purge", and "Aspiration On/Off" buttons and Battery Indictors. The "On/Off" button powers up the drive unit and touch screen interface LCD 62. Turning on power automatically moves the syringe armature mechanism 90 to be in a "home" position shown in FIG. 1.

In FIG. 1 the syringe armature 90 with moving syringe stage 58 with the auto-engage-aspiration thumb-pad receptacle 52, 56 is connected to the movable syringe armature, located on the top of the drive unit.

The top of the drive unit features a syringe cradle that includes detents or clamps 54 on the surface. These detents 54 engage the surface of the barrel of the syringe 18 as the syringe is placed within the syringe cradle to create an interconnection between the syringe and the syringe cradle.

Step 2: The drive unit 50 uses the disposable injection assembly 10 of FIG. 3, which comprises the following system components.

A syringe 18—the preferred embodiment uses a standard 20 cc syringe from Becton Dickinson, Inc. The design is not limited to a particular size or volume syringe. The operator will load the syringe with fluid from an appropriate sterile container, such as a multi-dose drug vial or single-use glass ampoule. The operator may fully load the syringe or partially load the syringe as the auto-detection feature determines the volume of fluid that is in the syringe.

The preferred embodiment uses the in-line pressure transducer 20—such as the Meritrans® in-line pressure transducer from Merit Medical, South Jordan, Utah. It is anticipated that the force sensor in the syringe armature could provide information corresponding to fluid pressure and negate the need for a secondary pressure sensor.

The subcutaneous hollow-bore needle 24 may be a Tuohy needle, such as the 20G×3.5" Tuohy Needle manufactured and sold by Becton Dickinson, Franklin Lakes, N.J. The sterile tubing set is 22-48" arterial pressure tubing, such as the sterile tubing sold by ICU Medical, Inc. of San Clemente, Calif.

The identification connector 12 may use any and all modalities of relaying and communicating to the CPU of the Drive Unit including but not limited to Infrared, Wi-Fi, Blue Tooth or other wireless modalities. The verification of the disposable assembly may also be accomplished using automated marking or labeling, such as applying a bar code to the injection assembly 10 and using a bar-code reader to scan the bar code. The bar code can incorporate an element that operates as a key so that when the system receives the bar code scan of an appropriate injection assembly, the system unlocks the drive unit 50 for use.

The identification connector 12 communicates to the CPU 80 of the drive unit to provide information related to the disposable injection assembly 10.

It is anticipated that additional information may be encrypted into the identification connector 12 such as, but not limited to: Drug information such as Drug Name and Formulation, Drug Manufacturer, Lot Number; Information related to the disposables assembles; Information related to expiration of dates for drug; Information related to sterility of disposable kit; and Date and time the ID-Connector was used.

Figure 7:
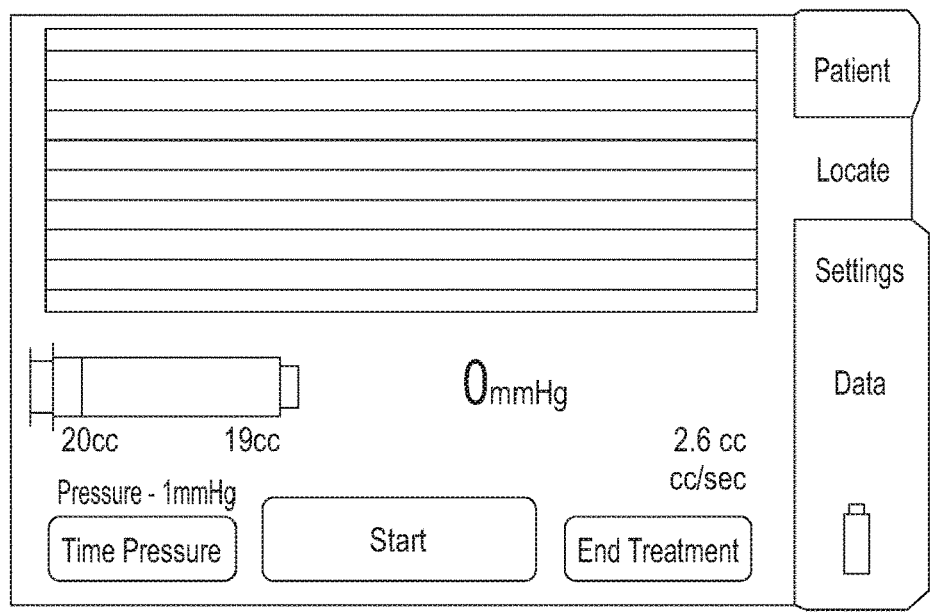
FIG. 7 is a screen shot of a display monitor of the drug delivery system illustrated in FIG. 1.

In a preferred embodiment, a 20 cc syringe 18 is connected to the Meritans pressure transducer 20 with an attached identification connector 12 and 48" Arterial Pressure Tubing set 22. At the distal end of the tubing set a Tuohy (hollow-bore) needle 24 is connected such in the FIGS. 1, 2 and 7.

Step 3: After the syringe 18 is inserted in the Syringe-Receptacle of the drive unit 50, the operator will view an initial screen 62 directing the operator to "Load Syringe and Press Continue". Touch screen interface 62 allows the operator to touch the "Continue" button which enables the Auto-Engage-Aspiration-Receptacle to make contact with the syringe thumb-pad.

Step 4: The operator inserts the needle into the patient at the target site. As the operator advances the needle, the system determines the feedback pressure at the needle and the visual signal generator projects a signal based on the determined pressure. The visual signal varies as the determined pressure varies. The operator continues to advance the needle using the visual signals from the visual signal generator to guide the insertion of the needle.

In the foregoing example, the feedback from the visual signal generator is based on the detected pressure. However, as noted above, the pressure relates to the flow rate of fluid from the syringe. Accordingly, it should be understood that the signal from the visual signal generator may be based, at least in part, on the fluid flow rate from the syringe to the patient.

The Auto-Syringe-Detection feature utilizes retention hooks of the Auto-Engaging-Aspiration-Receptacle to verify that the proper size syringe is selected. Confirmation is established by the size of the syringe thumb pad and the diameter between the hooks of the Auto-Engaging-Aspiration-Receptacle. If the syringe size and receptacle size are mismatched the hooks cannot engage. The loaded syringe may first be detected through a load cell contained in the drive unit syringe-armature. Forward motion of the syringe-armature is automatically stopped once resistance is detected on the syringe thumb-pad. The syringe-armature will then reverse direction after the spring-activated hooks engage the syringe thumb-pad. When a smaller diameter thumb-pad is used for a syringe size other than a 20 cc syringe the engaging hooks may not engage so that a syringe will not be detected. In response to the syringe not being detected, a warning message may be displayed or a signal made and further use of the drive-unit is prevented. For instance, the light assembly 100 may rapidly flash a red warning signal to prompt the operator to investigate the problem with the injection assembly.

The Auto-Syringe-Detection feature uses an optical and/or mechanical sensor to detect features of the syringe to thereby determine the volume of fluid in the syringe. The detected volume is displayed. Once detection of the syringe is completed and confirmed the system can automatically purge an appropriate amount of fluid into the tubing set to fully charge the disposable injection assembly 10.

In light of the foregoing and referring now to FIG. 11, an exemplary method of use will be described, which includes features of the visual signal generator 100 and the needle markings 344 along with counter head pressure for calculating the exit pressure. The following description is in connection with an epidural procedure, but it should be appreciated that the mehthodology may also apply to other processes, such as a peripheral nerve block procedure in which the fluid pressure in the needle is monitored.

Preliminarily, the operator prepares the instrument, setting up various parameters based on the details of the patient and the procedure. In the present example, a hand piece 300 having an epidural needle will be used. The needle has markings at defined distances, such as 1 cm sections that alternate silver and black colors. The operator connects the disposable tubing 22 and pressure sensor 20 to the syringe 18. The visual signal generator 100 is then directed at the patient so that the visual signal generator projects a beam of light onto the patient adjacent the intended site of the injection. The data the operator enters into the system will dictate the desired rate of insertion, which will also dictate the counter back pressure that will be part of the calculation when the system determines the exit pressure.

The drug delivery instrument 50 is started and a light is emitted from the visual signal generator 100. In this example a blinking light is emitted to provide a visual indication as to how quickly the operator is to advance the needle from one needle marking 344 to the next. For example the visual signal generator 100 will project a "Green" light upon the surface of the patient for 2 seconds and in that 2 second period the operator is to slowly advance the needle to the next marking on the needle at the surface of the patient. The light-emitting source will then go to "Black" for an instant (0.1 second). When the light turns "Green" again for the next two seconds the operator is to advance the needle another defined distance on the marked needle 344.

The operator continues to advance the needle into the patient tissue at the defined pace that is controlled by the blinking pattern. This pattern of 2 seconds of Green emitted light followed by a short blink of no light emitted continues as long as the pressure is ascending between points "A to B" on the graph in FIG. 11.

As the pressure rises between "A" to "B" the counter-head pressure value is included into the algorithm to adjust the exit-pressure value being displayed on the screen. During this period, the pressure rises so the light blinks green.

The visual indication that the light is blinking Green at a defined rate alerts the user of two aspects of the system: 1) That the needle is to be inserted at a specific pace of needle insertion by coordinating the pace of penetration of the skin (which in turn provides the instrument a constant, known value for counter-head-pressure). 2) It alerts the operator that pressure is ascending between 0 mm/Hg to 100 mm/Hg in this example. During this period the drive unit may be expelling fluid from the syringe through the needle.

The operator continues to advance the needle into the patient toward the target, which in this example is the ligamentum flavum when performing an epidural injection.

Figure 11:
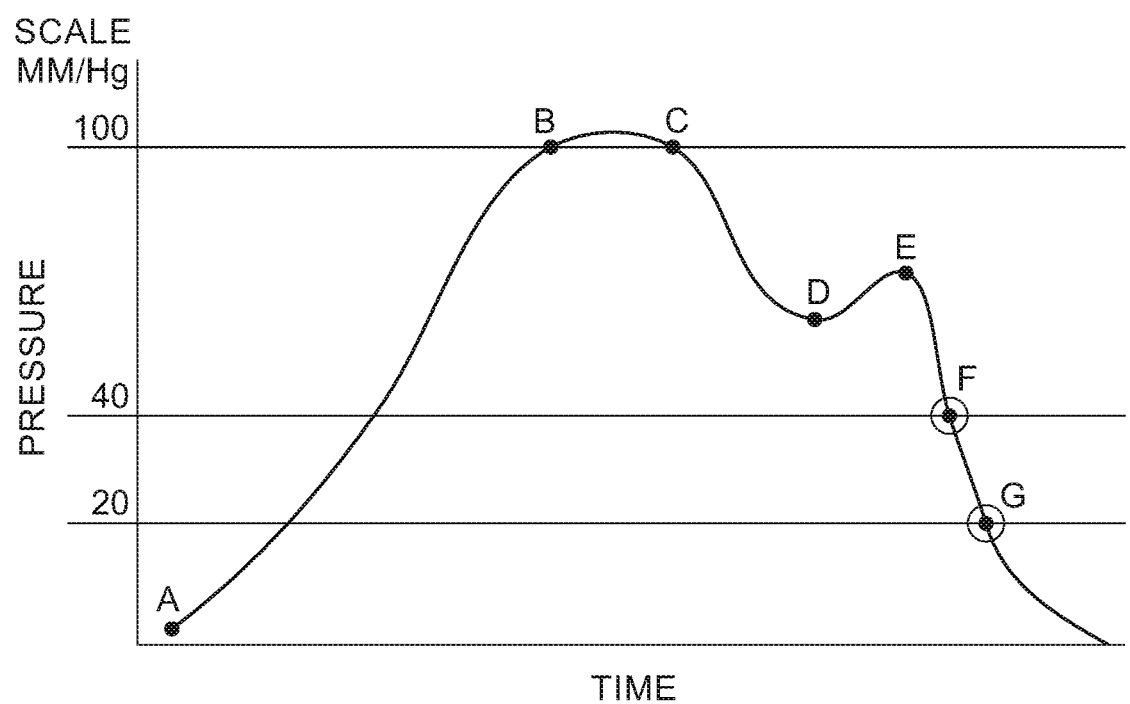
FIG. 11 is a graphical representation of fluid pressure versus time during needle insertion for an epidural procedure using the drug.
Figure 12:
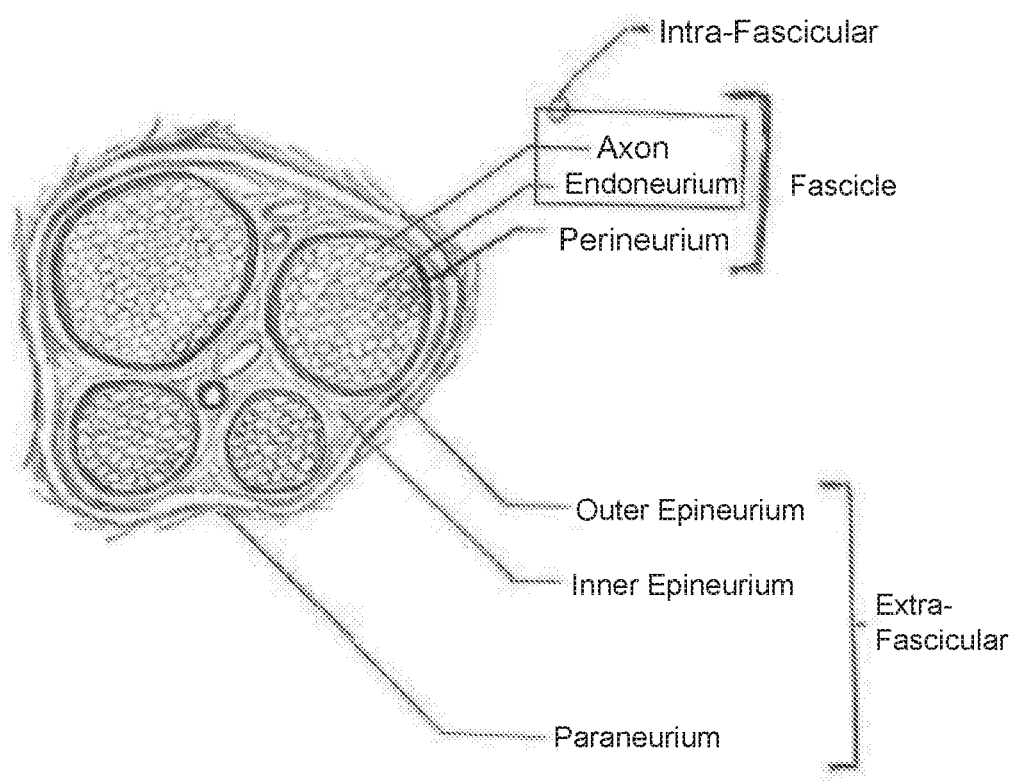
FIG. 12 is a cross-section view of a fascicle of nerve fibers.

When the pressure reaches the point "B" on FIG. 11, the motor of drive unit 50 stops because the fluid pressure reached the pre-defined pressure limit that was pre-programmed. When the motor stops, the drive unit no longer is expelling medication from the syringe. When it reaches this pre-defined value the instrument discontinues the indication of needle insertion rate via a blinking emitted light.

This value but can be changed if desired by the operator (in this case it is pre-set to 100 mm/Hg).

When point "B" is reached a specific emitted visual alert is provided. This may be the use of a different color, in this example a White emitted Light. This light may be constant or blinking to represent that the maximum pressure has been reached.

Although the pressure remains at 100 mm/Hg between point "B" and "C" for a period of time there is no additional visual information related to needle movement. The operator can look on the screen if so desired to see that a pressure value is at 100 mm/Hg.

The operator continues to advance the needle so that the tip of the needle enters the epidural space at point "C". A drop in pressure occurs as the needle enters the epidural space and the motor of the drive unit 50 starts to displace the plunger, thereby expelling medication from the syringe. Nonetheless, the pressure will decrease during this time between "C" to "D". The light emitting source will provide a blinking RED light to indicate that a descending pressure is occurring.

At Point "D" the pressure reaches an inflexion point and begins to increase once again. At point "D" the emitted light indictor changes between points "D" to "E" to be represented by a Blinking Green Light that blinks at a defined 1 second pace which distinguishes it from the needle insertion pace between Points "A" to "B".

At inflexion point "E" the pressure once again starts to decrease at which point the visual signal generator changes once again to a blinking RED light until a predefined discreet pressure value at point "F" is detected.

After reaching Point "F" and the pressure drops below 40 mm/Hg pressure value, a solid RED Color is emitted between Points "F to G" to indicate that the exit-pressure value is between 40 mm/Hg to 20 mm/Hg.

Once the pressure passes Point "G" the pressure drops to the 20 mm/Hg pressure value and a solid BLUE color is emitted to indicate that a minimal pressure value has been reached and the exit-pressure value is between 20 mm/Hg and Zero mm/Hg.

At this time the identification of the epidural space is confirmed by the operator and the use of the instrument is concluded.

Infusion System with Electrical Stimulation

Figure 13:
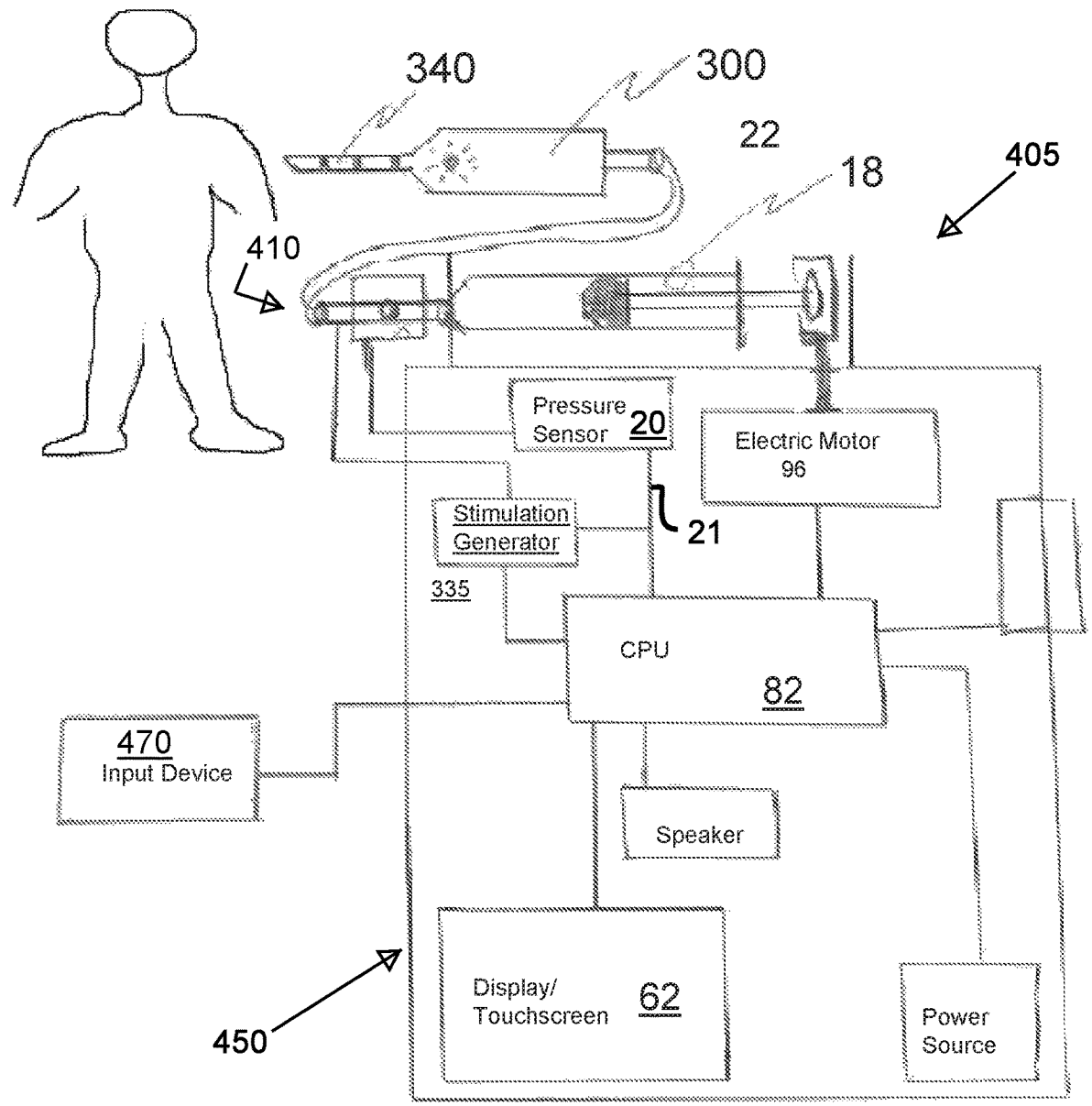
FIG. 13 is side view of an injection device of the drug delivery system illustrated in FIG. 2.

Referring to FIGS. 10 and 13 a drug infusion system that includes electrical stimulation elements is designated 405. The system 405 is configured to be used in various procedures, such as a peripheral nerve block. The system 405 includes numerous elements that are the same as or similar to elements described above in connection with the system designated 5. Accordingly, elements in system 405 that are substantially similar to elements in system 5 include the same reference numerals.

The system 405 includes an injection assembly 410 and a computer-controlled drug delivery instrument 450 similar to the injection assembly 10 and drive unit 50 described above. The injection assembly 410 includes an insertion needle 340 and is connected with the drive unit 450, which controls the flow of fluid to the injection assembly during use. The system 405 also includes one or more output mechanisms that provide data to the medical professional during a procedure to assist in proper placement of the needle in the subject.

The system 405 is operable to determine the location for an intra-fascicular needle location. The system is also operable to deliver therapeutic medication to an intra-fascicular needle location. The medication may include, but is not limited to local anesthetic solutions, such as, cortico-steroids, hydroxyapatite, joint replenishment drugs, sclerosing agents and other drugs that are typically injected into a fluid-filled tissue space for therapeutic purposes.

An intra-fascicular needle location is one in which the tip of the needle penetrates through the perineurium so that the needle tip is located inside the fascicle. An extra-fascicular needle location is a position in which the needle is anywhere outside the perineurium of an individual fascicle, which may include outside the outer epineurium or even the paraneurium thereby defined as completely extraneural.

Irreversible damage can occur to a nerve when the needle tip is both embedded into a fascicle and then fluid under hydrostatic pressure produces changes to the neural and vascular tissues within the fascicle. This occurs because the outer layer of the fascicle is a protective layer of a relatively non-compliant, rigid protective structure. This protects the basic components of the nerve, the axons, which are densely packed within the fascicle. In other words, the fascicle represents a densely packed arrangement with a thick protective shell. The fascicle does not readily deform by either expanding or contracting. Therefore, tissue compliance to an inflow of fluids is extremely low and/or non-existent. Needle penetration into the fascicule may not necessarily cause the ultimate damage to the axon units, but the combined effect of needle penetration and increased pressure inside the fascicle from the infusion of fluids inside the fascicle can produce damage to the capillary bed. Additionally, fluid pressure-induced strangulation of the microcirculation of the axons impedes short-term nutrient replenishment after such physical trauma thus leading to initial necrosis. The cascade from necrosis leads to an inflammatory response in an effort to initiate a wound healing from the initial pressure-induced trauma further advancing or cascading potentially toward irreversible damage.

However, there are instances in which intentional intra-fascicular needle placement is desirable and required. Such instances include unresolved phantom pain after a limb is removed. Additionally, hyperactive neural stimulation of a particular limb may sometimes lead to retractable pain and is another circumstance in which intentional intra-fascicular needle location and delivery of agents is required. Accordingly, the system 405 and its use provide a method and apparatus for effectively discriminating between the extra-fascicular and intra-fascicular location of a needle.

Injected fluid disperses through tissue at different rates. As a result, the fluid pressure varies. Therefore, this fluid pressure (or an internal pressure related to the resistance pressure of a tissue) is indicative of, and may be used to identify several types of tissues.

The system 405 enables a practitioner to accurately identify fluid-filled tissue space while limiting the placement of drugs into non-targeted tissues. This is performed for both diagnostic and therapeutic procedures. The system 405 utilizes the pressure of a fluid from a needle or catheter following placement of the needle/catheter within the tissue in order to identify the accuracy of placement and to monitor the placement during an injection or aspiration.

Specifically, the system 405 includes one or more output mechanisms for providing audible and/or visual feedback of the detected fluid pressure in the insertion needle. The operator uses the visual feedback as guidance during the placement of the insertion needle. As shown in FIG. 13, the first output mechanism may be a video display screen, such as an LCD display for displaying data to aid the operator. Additionally, a second output mechanism may also be provided. For example, the second output mechanism may be a speaker for providing an output signal.

The system 405 includes a injection assembly 410 that includes a syringe 18 and an elongated length of flexible tubing 22 having a first end connected with the syringe and an insertion needle 340 connected with the second end. In this way, fluid from the syringe can be expelled through the tubing 22 and into the needle 24. The injection assembly 410 also includes a pressure sensor for detecting fluid pressure in the injection assembly. The pressure sensor may be disposed in one of several locations to measure a pressure that correlates with the fluid pressure at the tip of the needle 340. In the present instance, the pressure sensor 20 is an inline fluid pressure sensor attached to the syringe 18 between the syringe and the tubing 22. In this way, the pressure sensor 20 senses the fluid pressure as the fluid exits the syringe and enters the tubing 22 to which the insertion needle 340 is connected.

The injection system 410 may also include a re-useable hand-piece 300 to which the needle is attached. As shown in FIG. 10, the insertion needle 340 is connected to the forward end of the hand piece and the tubing 22 is connected to the rearward end of the hand piece. The hand piece 300 may include features that assist the operator during the insertion process, as described further below. Additionally, the hand piece 300 may be configured to provide electrical stimulation as discussed further below.

The injection assembly may be manually operated to inject fluid. However, in the present instance, a computer-controlled drug delivery system 450 controls the flow of fluid from the injection assembly as discussed further below. An output cable 21 connects the pressure sensor 20 with the drug delivery system 450 so that the drug delivery system can monitor and, if desired, vary the flow of fluid from the syringe in response to the data from the pressure sensor 20. The pressure-transducer 20 may be connected inline between the forward end of the cylinder of syringe 18, and the first end of tubing 22. One exemplary connection is a Luer connection for connecting the pressure-transducer 20 to the tip of the syringe. The connection may be fixed by a threaded connection and/or an irreversible threaded connection, such as a LuerLok. Alternatively, the pressure transducer 20 may be permanently fixed to the syringe by plastic welding or chemical binding, such as adhesive. In this way, the instantaneous, actual fluid pressure in the drug delivery line 22 is sensed and used by the instrument, thereby providing a close approximation to the actual, instantaneous fluid pressure at the point or tip of the needle 340, and therefore, at the location in the patient's body where the needle tip is located. The electronic pressure-transducer 20 provides pressure data via electronic data cables that are connected directly to the central unit 50 to collect the pressure measurements.

As described above, the system 405 may include a fluid delivery system 50 for providing a controlled flow of medication to the injection assembly 10. Preferably the fluid delivery system is an automated system and in the present instance is a computer controlled fluid delivery system referred to as a drive unit 450 which operates similar to drive unit 50 described above unless mentioned otherwise in the following description.

Electrical Stimulation

The system 405 may also include an electrical stimulation element 334 for providing electrical nerve stimuli to a target tissue in a patient. The electrical stimulation element is a conductive element connected with the hand piece 300. The electrical stimulation element is operable to provide an electrical charge of low intensity (i.e. approximately 0.15 mA up to approximately 2.0 mA) and short duration (i.e. pulses of approximately 0.1 to 1 Ms). The electronic stimulation elements provide the stimuli for a short time (i.e. approximately 1-10 seconds).

The electric stimulator may be an external element or an internal element. For example, FIGS. 10 and 13 illustrate an embodiment that incorporates external electric stimuli. A conductive element 334 such as an electrically conductive cable interconnects the hand piece 300 with a stimuli generator 335, so that electrical stimuli are transmitted to the hand piece from the stimuli generator. In turn, the hand piece is connected with an element configured to deliver the electrical charge to the tissue. For instance, the needle 340 may be formed of electrically conductive material and the hand piece may include a connection with the needle providing an electrical pathway from the conductive element and the needle. Alternatively, a conductive element, such as a wire, may extend along the length of the needle and the needle may be electrically insulated from the needle. For example, the needle may be formed of electrically insulative material. An example of an external electric stimulation element is the insulated needle sold under the trade name "Stimuplex®" or the over the needle catheter sold under the trade name "Contiplex®C" by B. Braun Medical Inc. of Bethlehem, Pa.

Alternatively, the system may utilize internal electric stimuli. For example, the fluid injected from the syringe may be an ionic solution capable of conducting electric stimuli. A conductive element may be interconnected with the fluid within an insulated needle. The needle may be constructed from a variety of non-conductive materials. For instance, the conductive element may project into the fluid path at some point between the syringe 18 and the needle 340. For example, the conductive element may impart the electric stimuli into the fluid at the rearward end of the hand piece 300. If the electric stimuli are imparted to the tissue via the fluid, the needle 340 may be electrically insulated to minimize any drain or disbursement of the electric charge through the sidewalls of the needle.

The electrical stimulation element is connected with an electric stimuli generator 335, which is an electrical source operable to provide an electrical charge or pulse to the stimulation element. The stimuli generator may be incorporated into the drive unit 450 as shown in FIG. 3. In such an arrangement the stimuli generator 335 is connected with the CPU of the drive unit so that the CPU provides electric signals to control the operation of the stimuli generator. Alternatively, the stimuli generator may be a separate element having a separate power source and separate control.

The system 405 may also include a user operable input mechanism 470, which allows the operator to provide an input signal for controlling the system. The input mechanism may be any of a variety of devices, such as a handheld or foot operated control that provides a means for the operator to start, stop, and change the flow-rate from a single flow-rate to a second or third distinct pre-set flow rate. Alternatively, the input element may be a button, touchscreen, mouse, keyboard or a microphone for providing input commands audibly. Additionally, the system may include a plurality of input mechanisms to allow the operator to input a variety of inputs for various stages of a procedure. For example, the system may include a first input mechanism, such as a foot pedal that controls the flow of fluid through the device. Actuating the foot pedal switch (i.e. depressing the switch) sends a signal to the CPU of the drive unit, which in turn sends a signal to the motor to drive the motor so that fluid flows from the syringe to the needle 340 as long as the pedal is actuated. Alternatively, actuating the foot pedal a first time may operate a start signal to start the fluid flow and the fluid may continue to flow until the operator actuates the foot pedal again. In this way, the second actuation operates as a stop signal to discontinue the fluid flow. Additionally, the system may include a second input mechanism, such as a touch screen, so that once an electronic simulation is applied to a patient the operator may input an indication of whether or not muscle twitch was detected or whether a sensation is noticed by the patient. Further still, the primary or secondary input mechanism may be a control button, such as button 325 on the hand piece. Actuating the control button 325 may send a signal to the CPU to provide a response input during a procedure.

As discussed above, the fluid pressure is used to control operation of the system 5. Similarly, fluid pressure is used to control operation of the peripheral nerve block system 405. For instance, the system 405 may provide a signal to the operator when the fluid pressure exceeds a threshold, thereby indicating that the needle may be located intra-fascicularly. As discussed above, there are several methodologies for calculating the fluid pressure at the exit of the needle.

Method of Operation of System Incorporating Electrical Stimulation

An exemplary method for administering an epidural injection using the system described above will now be described. It should be understood that the present system is not limited to use in peripheral nerve block procedures. Accordingly, it should be understood that the principles and methods described below may be readily adapted for injections into tissues and anatomical areas in a variety of applications and procedures.

The system may be used to detect whether the needle is positioned within the fascicle (i.e. positioned intra-fascicularly). The system makes the determination based on a combination of several variables. First, if the needle has pierced the endoneurium the fluid pressure will be quite high because the axons are tightly packed within the endoneurium. Additionally, if the needle has pierced the endoneurium the operator is likely to observe a noticeable response to an electrical stimulation applied to the patient at or adjacent the needle tip. Therefore, if the operator notices a high fluid pressure and then applies an electrical stimulation and notices a response, it is likely that the needle is positioned intra-fascicularly and therefore should be re-positioned. Therefore, the system may operate as follows.

Figure 14:
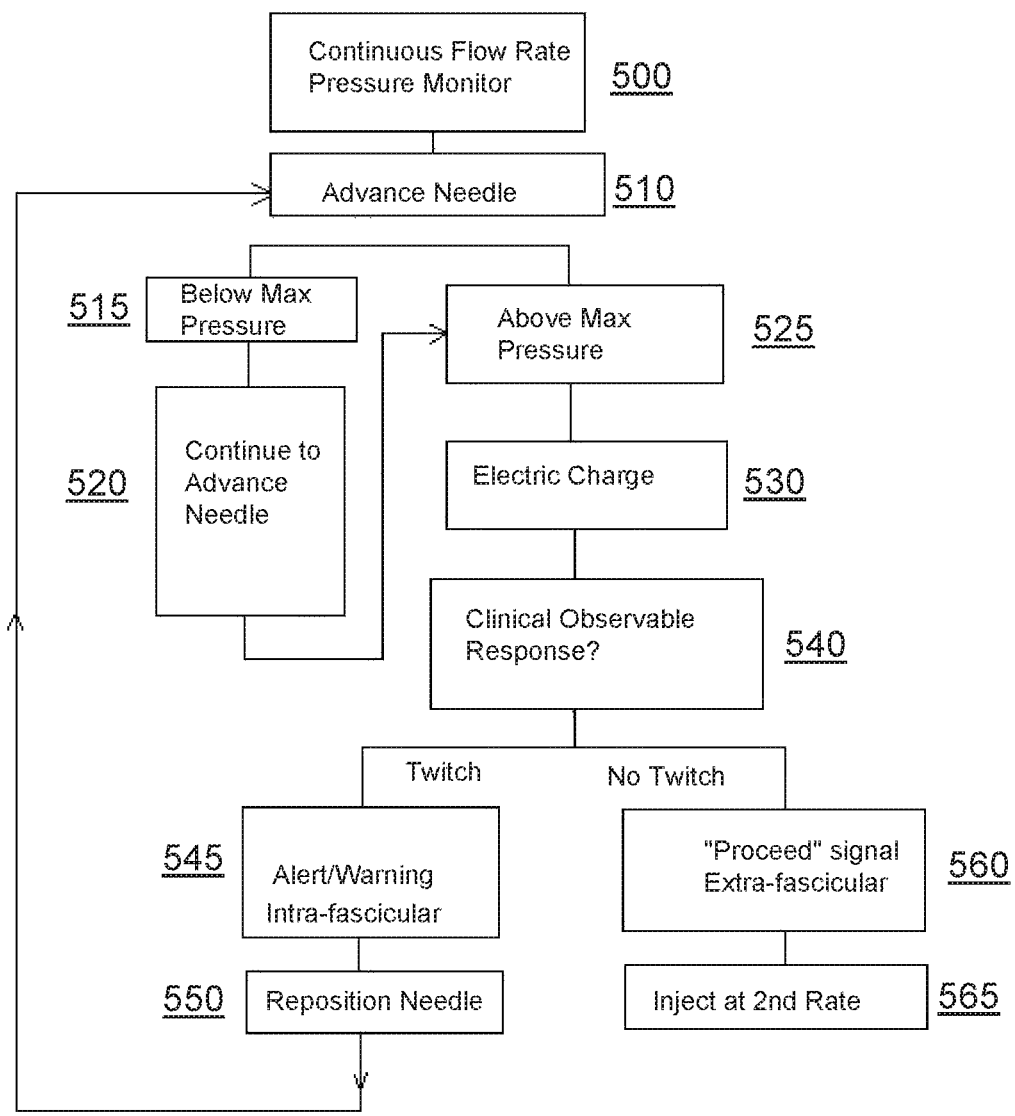
FIG. 14 is a flow chart of a method for injecting fluid.

Referring to FIG. 14, at step 500 the operator selects the procedural parameters, such as the upper threshold and/or the fluid flow rate and/or the rate of needle advancement. For example, the operator may set an upper threshold pressure, such as 300 mm/Hg. Alternatively, the upper threshold may be pre-set in the system when the operator selects the type of procedure for which the system is to be used. Similarly, the operator may select the fluid flow rate through the needle or the flow rate may be set automatically when the operator selects the type of procedure. Additionally, the operator may select the duration of the electrical nerve stimulation when it is applied. Once the procedural parameters are selected, the operator provides an indication that the procedure is to start. For instance, the operator may press a start button on the drive unit.

At step 510 the operator advances the needle into the patient. As discussed above, the needle may be advanced at any of a variety of insertion rates, such as 3 to 10 mm/sec. Preferably, the needle is inserted at a substantially constant rate. Accordingly, at step 510, the operator may insert the needle at a constant rate being guided by the indicator 315 as described above.

At step 515 as the operator advances the needle, the system continuously determines the feedback pressure at the needle and provides feedback either visually or audibly regarding the determined pressure. The visual signal varies as the determined pressure varies.

At step 520 the operator continues to advance the needle as long as the system does not provide a signal indicating that the fluid pressure has exceeded the upper limit.

At step 525 the fluid pressure exceeds the upper threshold so the system provides a warning signal in the form of an audible, visual and/or tactile signal. In response to the signal indicating that the fluid pressure exceeded the upper threshold, the operator stops advancing the needle. Additionally, the drive unit may stop the motor to stop the flow of fluid to the needle.

At step 530 an electrical nerve stimulation signal is applied at or adjacent to the tip of the needle 340. For instance, as described above, an electrical nerve stimulation can be applied to a conductive element positioned adjacent the needle tip. The electric nerve stimulation may be provided automatically by the system in response to the fluid pressure exceeding the upper threshold. For instance, one the fluid pressure exceeds the upper threshold the system provides a signal to the operator. Additionally, at that point or after a short delay, such as 1-3 seconds, the system may provide the electrical nerve stimulation. Alternatively, the operator may apply the electric stimuli by providing an input prompt, such as pressing a button or providing a verbal command. In response to the operator's prompt, the electric nerve stimulation is applied to the patient. In other words, when the fluid pressure exceeds the upper threshold the system prompts the operator to apply the electric charge and in response to the signal the operator applies the electric charge.

At step 540 the operator monitors the patient to detect any clinically observable response, such as a muscle twitch. The operator then provides an input to the system indicative of whether an observable response was detected or not. For instance, the operator may press a first button if the operator noticed a twitch or the operator may press a second button if the operator did not notice a twitch. If the operator noticed an observable response then method proceeds to step 545. If the operator did not notice an observable response then the method proceeds to step 560.

At step 560 the system provides an alert warning to the operator. The alert may be visual, audible and/or tactile. The warning warns the operator that the needle may be positioned intra-fascicularly. For example, the system may provide an audible warning sound, such as the word "warning", while also providing a flashing light on the hand piece.

At step 550 the operator withdraws the needle and repositions the needle in an attempt to place the needle in the target area without piercing the perineurium. In this way, the method re-starts at step 510.

If no observable response it detected at step 540, the method proceeds to step 560. At step 560 the system provides a signal to the operator indicating that the needle is properly located for an injection (i.e. the needle tip is located extra-fascicularly). For example, the drive unit 50 may provide an audible signal such as announcing the word "proceed" or providing a visual signal, such as the word "proceed" on the display screen of the drive unit or the hand piece.

At step 565 the flow rate of fluid is increased to a second rate that is higher than the first rate. The operator may inject a preliminary amount that may be observable so that the operator may detect that the needle is properly placed. Once placement is verified, the operator may inject a bolus of fluid to anesthetize the patient. Alternatively, the operator may inject the bolus of fluid without first injecting an amount to verify the needle placement. Either way, a quantity of fluid is injected at step 565 at a higher rate than the previous low flow rate. Alternatively, in response to an indication that the upper pressure limit was exceeded and an indication that no response was observed in response to the electric nerve stimulation, the drive unit may automatically increase the flow rate, such as by increasing the speed of the motor Another feature of the current device and methodology is the objective nature of pressure measured by a computer-controlled drug delivery device that is monitored during all phases of the injection process. The clinician, therefore, no longer relies on the subjective nature of a "feel" but rather is provided with objective information of absolute values while performing each phase of this critical technique. Each phase of the technique is improved by the ability to objectively monitor the pressure on a continuous basis.

It should be understood that the example of 300 mm/Hg as the maximum pre-set pressure for stoppage of fluid flow is an example and that either a lower or higher pre-set pressure may be selected at the discretion of the clinician. The techniques described herein are equally applicable to human and animal tissues.

It will be recognized by those skilled in the art that changes or modifications may be made to the above-described embodiments without departing from the broad inventive concepts of the invention. For instance, in the foregoing description, the system is described in the context of providing fluid infusion. However, it should be understood that the system may be used for placement of a needle to aspirate fluid-filled tissue. Specifically, the injection device may be used for aspiration of a fluid-filled tissue space after the identification of a fluid-filled space is determined. Aspiration may be used either to withdraw a sample of tissue or extracellular fluid (i.e., cerebral spinal fluid, intra-articular fluid, blood, etc.), or may be used to determine the correct placement of the injection needle. During an aspiration procedure, the "entry pressure" is measured in the same manner as the pressure within the fluid-filled tissue space, which is characterized by a loss of pressure. Likewise, false loss of pressure is also identified using an aspiration procedure because the internal tissue structure (i.e., cyst) will be quickly drained of its contents and the entry pressure will rise above the threshold entry pressure.

It should therefore be understood that this invention is not limited to the particular embodiments described herein, but is intended to include all changes and modifications that are within the scope and spirit of the invention as set forth in the claims.

What is claimed is:

1. An apparatus for aiding a user in advancing a needle into a mammalian subject at a selected insertion rate, the apparatus comprising:
   a needle having a plurality of markings along the length of the needle;
   a fluid reservoir in fluid communication with the needle;
   a sensor configured detect a characteristic indicative of a fluid pressure in the needle;
   an indicator element configured to emit one or more of an audible and visual signal at a selected cadence correlated to the selected insertion rate; and
   a microprocessor disposed in communication with the sensor to receive the characteristic indicative of the fluid pressure in the needle, and the microprocessor in electrical communication with the indicator element to provide a signal repeating at the selected cadence to actuate the indicator element at the selected cadence, whereby the user can insert the markings on the needle at the selected insertion rate in response to the selected cadence of the one or more audible and visual signals.

2. The apparatus of claim 1 wherein the fluid reservoir comprises a syringe barrel.

3. The apparatus of any of claim 1 wherein the markings on the needle are uniformly spaced apart from one another along the length of the needle.

4. The apparatus of claim 1 wherein the markings are equidistant from one another along the length of the needle.

5. The apparatus of claim 1 wherein the selected cadence occurs at a recurring frequency.

6. The apparatus of claim 5 wherein the frequency corresponds to the selected insertion rate so that the indicator signal guides the rate of insertion of the needle.

7. The apparatus of claim 1 wherein the indicator element comprises a light element.

8. The apparatus of claim 7 wherein the visual signal flashes or blinks according to a frequency correlated to the selected insertion rate.

9. The apparatus of claim 8 comprising a handle connected to the second end of the tubing wherein the light element is mounted on the handle.

10. The apparatus of claim 1 wherein the selected cadence is correlated to a known counter-head pressure, and the microprocessor is configured to calculate an exit-pressure of fluid from the needle based on the known counter-head pressure and the fluid pressure in the needle.

11. The apparatus of claim 10 wherein the microprocessor is configured to subtract the known counter-head pressure from the fluid pressure in the needle.

12. The apparatus of claim 10 wherein the needle is provided in a handpiece having a switch mounted thereto, the switch in communication with the microprocessor and operable to provide a first signal to the microprocessor indicating that the real-time exit-pressure should be adjusted by the known counter-head pressure.

13. The apparatus of claim 12 wherein the switch is operable to provide a second signal to the microprocessor indicating that the real-time exit-pressure should not be adjusted by the known counter-head pressure.

14. The apparatus of claim 12 wherein the first signal to the microprocessor indicates that the known counter-head pressure should be added to the fluid pressure in the needle.

15. The apparatus of claim 12 wherein the first signal to the microprocessor indicates that the known counter-head pressure should be subtracted from the fluid pressure in the needle.

\* \* \* \* \*